(12) United States Patent
Kim et al.

(10) Patent No.: US 12,398,395 B2
(45) Date of Patent: Aug. 26, 2025

(54) DNA APTAMERS FOR PANCREATIC CANCER DETECTION

(71) Applicants: JP BIO A INC., Seongnam-si (KR); NATIONAL CANCER CENTER, Goyang-si (KR)

(72) Inventors: Yun Hee Kim, Goyang-si (KR); Kyun Heo, Seoul (KR); Sun Il Choi, Goyang-si (KR); In Hoo Kim, Goyang-si (KR)

(73) Assignees: JP BIO A INC., Seongnam-si (KR); NATIONAL CANCER CENTER, Goyang-si (KR)

(*) Notice: Subject to any disclaimer, the term of this patent is extended or adjusted under 35 U.S.C. 154(b) by 1063 days.

(21) Appl. No.: 17/416,858

(22) PCT Filed: Aug. 8, 2019

(86) PCT No.: PCT/KR2019/009956
§ 371 (c)(1),
(2) Date: Jun. 21, 2021

(87) PCT Pub. No.: WO2020/130269
PCT Pub. Date: Jun. 25, 2020

(65) Prior Publication Data
US 2022/0090081 A1 Mar. 24, 2022

(30) Foreign Application Priority Data
Dec. 21, 2018 (KR) .......................... 10-2018-0167948

(51) Int. Cl.
*C12N 15/115* (2010.01)
(52) U.S. Cl.
CPC ........ *C12N 15/115* (2013.01); *C12N 2310/16* (2013.01); *C12N 2310/321* (2013.01); *C12N 2320/13* (2013.01)
(58) Field of Classification Search
CPC .............. C12N 15/115; C12N 2310/16; C12N 2310/321; C12N 2320/13
See application file for complete search history.

(56) References Cited

U.S. PATENT DOCUMENTS 6,582,908 B2 * 6/2003 Fodor .................... C07H 21/00
506/30

FOREIGN PATENT DOCUMENTS

| EP | 2481800 A2 | 8/2012 |
|---|---|---|
| KR | 10-1189790 B1 | 10/2012 |
| KR | 10-1250557 B1 | 4/2013 |
| KR | 10-1568400 B1 | 11/2015 |
| KR | 10-1699105 B1 | 1/2017 |

OTHER PUBLICATIONS

Hori, S. I., Herrera, A., Rossi, J. J., & Zhou, J. (2018). Current advances in aptamers for cancer diagnosis and therapy. Cancers, 10 (1), 9. (Year: 2018).*
Ruiz Ciancio, D., Vargas, M. R., Thiel, W. H., Bruno, M. A., Giangrande, P. H., & Mestre, M. B. (2018). Aptamers as diagnostic tools in cancer. Pharmaceuticals, 11(3), 86. (Year: 2018).*
Sun, H., Zhu, X., Lu, P. Y., Rosato, R. R., Tan, W., & Zu, Y. (2014). Oligonucleotide aptamers: new tools for targeted cancer therapy. Molecular Therapy-Nucleic Acids, 3. (Year: 2014).*
Rialon et al., "Aptamers: Potential Applications to Pancreatic Cancer Therapy", Anti-Cancer Agents in Medicinal Chemistry, 2011, vol. 11, No. 5, pp. 434-441 (8 pages total).
Extended European Search Report dated Sep. 26, 2022, in European Application No. 19900348.4.
Pooja Dua et al., "Alkaline Phosphatase ALPPL-2 Is a Novel Pancreatic Carcinoma-Associated Protein", Therapeutics, Targets, and Chemical Biology, Cancer Research, Mar. 15, 2013, pp. 1934-1945, vol. 73, No. 6.
Dion A. Daniels et al., "A tenascin-C aptamer identified by tumor cell SELEX: Systematic evolution of ligands by exponential enrichment", PNAS, Dec. 23, 2003, pp. 15416-15421, vol. 100, No. 26.
International Search Report of PCT/KR2019/009956 dated Oct. 30, 2019 [PCT/ISA/210].
Inhu Kim, "Development of New-concept Anti-tumor Drugs through Construction of Aptamer-antibody Complex Platform Technology", Research Report, National Cancer Center, Nov. 10, 2016, pp. 1-39.

* cited by examiner

*Primary Examiner* — Jennifer Dunston
*Assistant Examiner* — Christina Tran
(74) *Attorney, Agent, or Firm* — Sughrue Mion, PLLC

(57) ABSTRACT

Provided are DNA aptamers selected from a DNA library using Cell-SELEX to bind specifically to cancer cells, which are optimized for high binding affinity to cancer cells can be effectively used for the diagnosis of cancer as they have enhanced targeting efficiencies for target cells and tissues as well as high serum stability.

6 Claims, 27 Drawing Sheets
Specification includes a Sequence Listing.

Enrichment of aptamer pool at 5th Round

FIG. 3
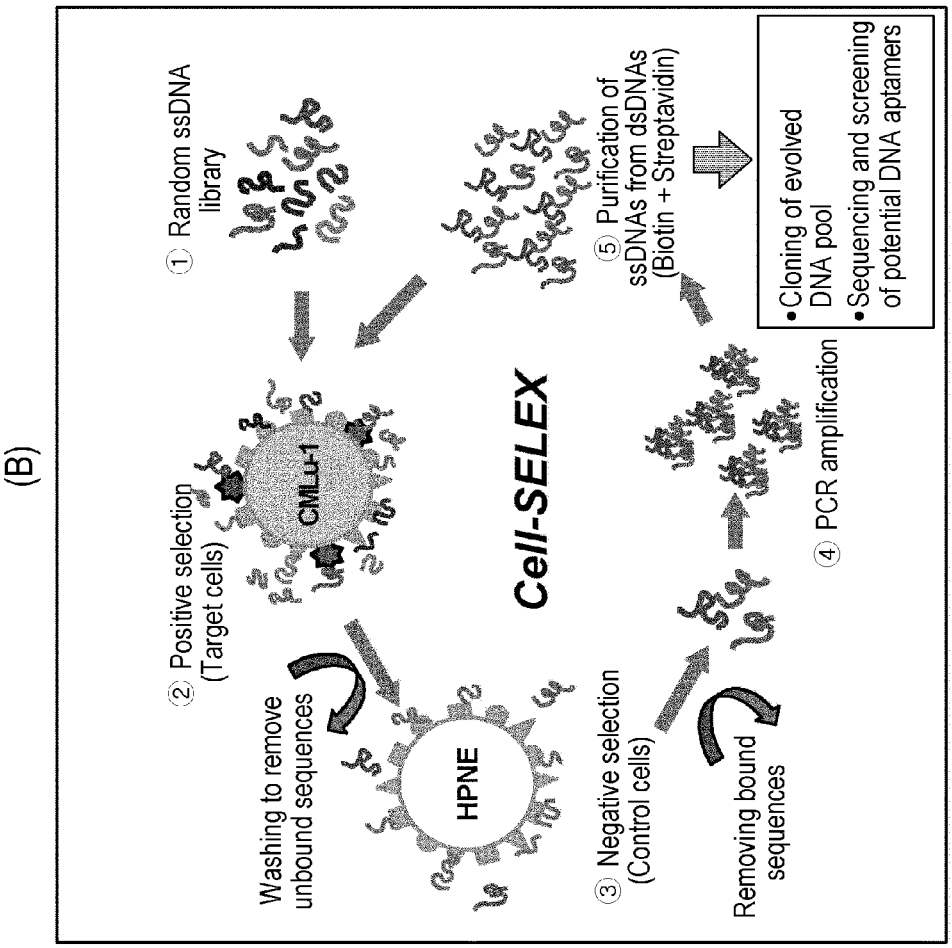
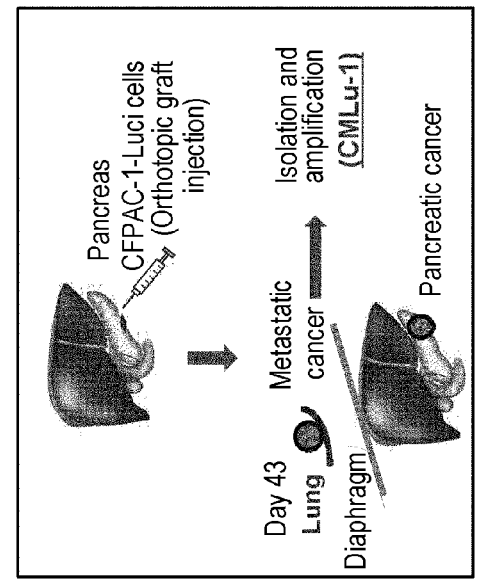
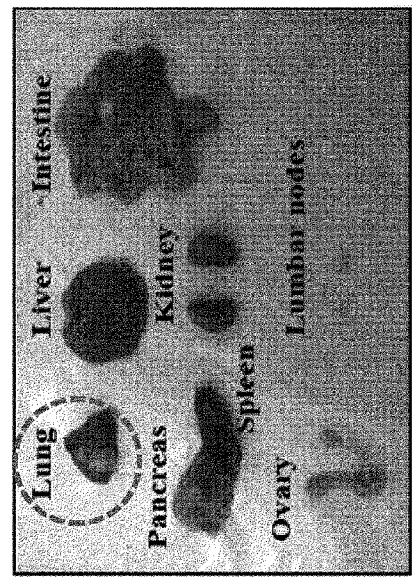

Structure of SQ7
(SEQ ID NO: 4)

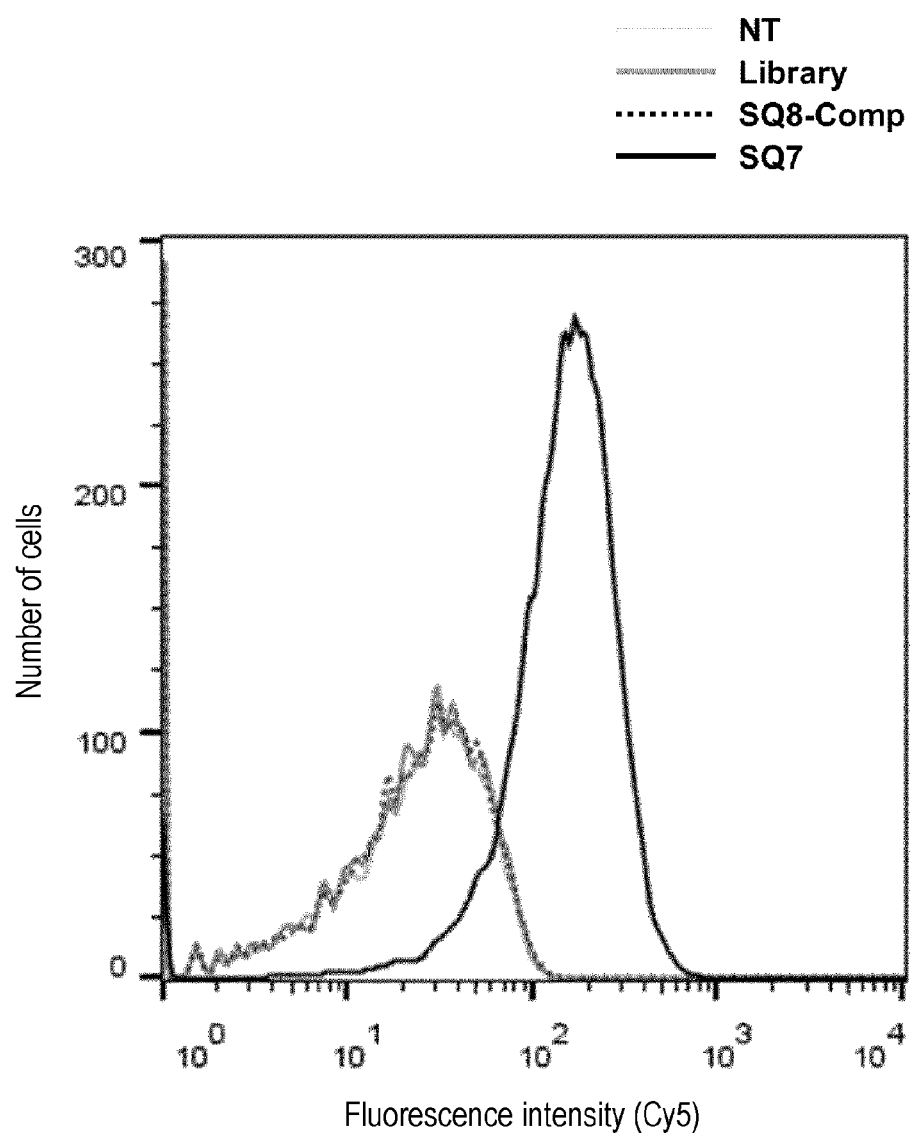

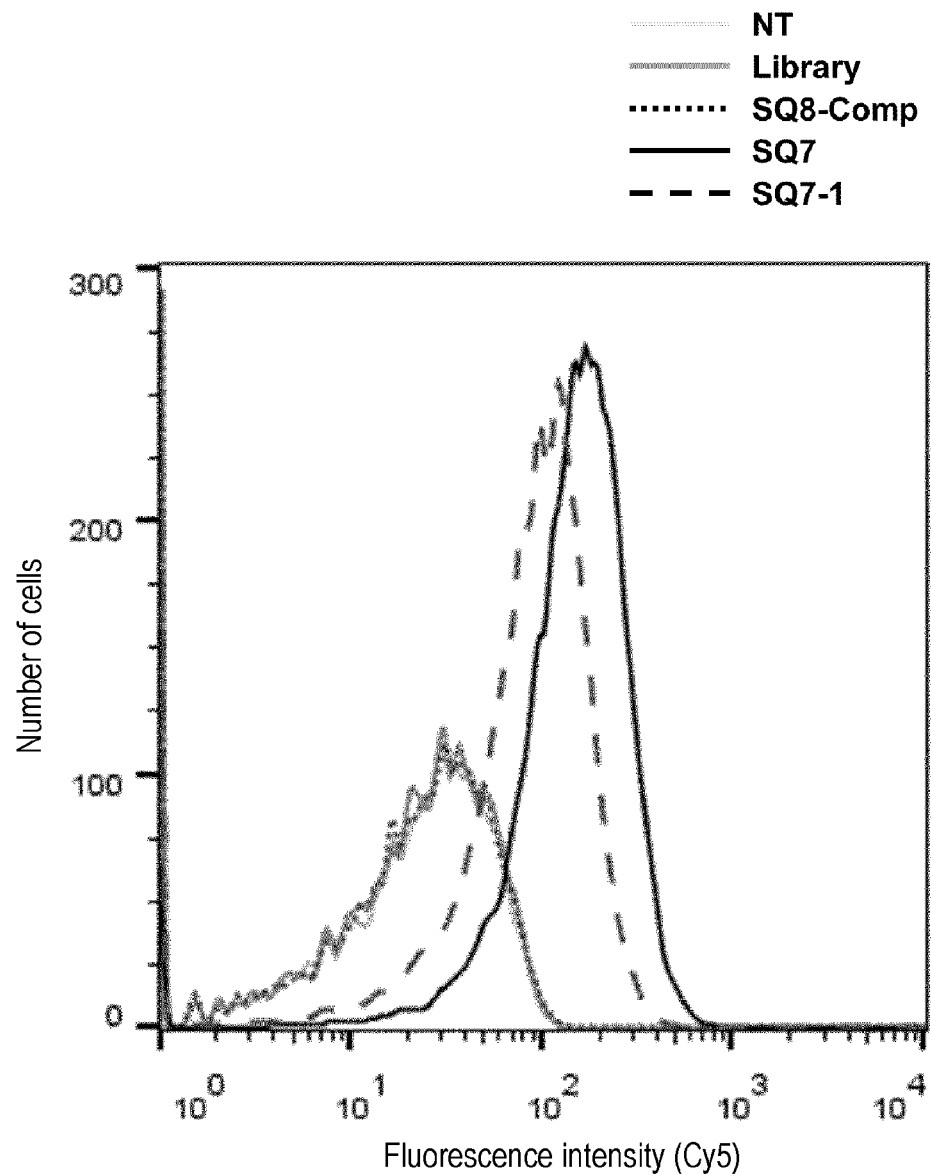

FIG.7
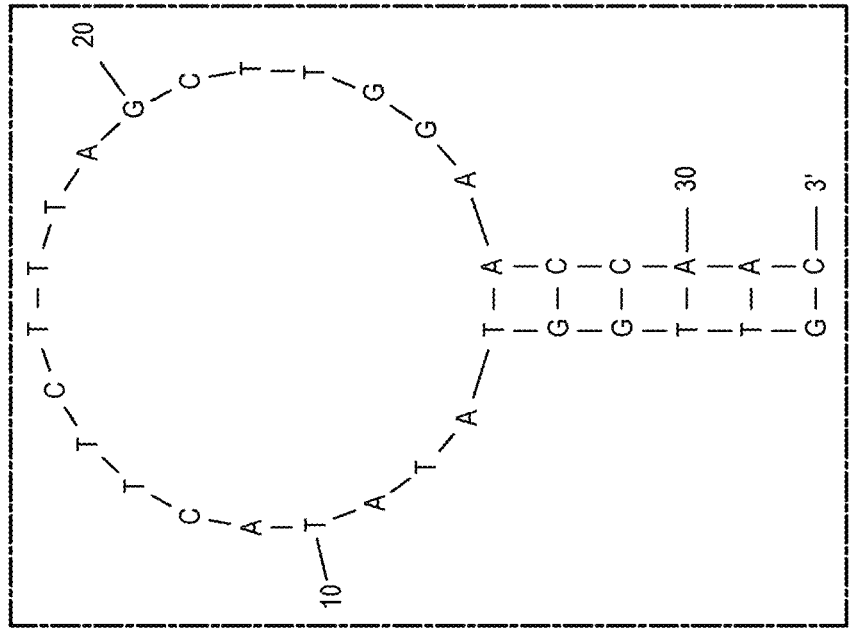
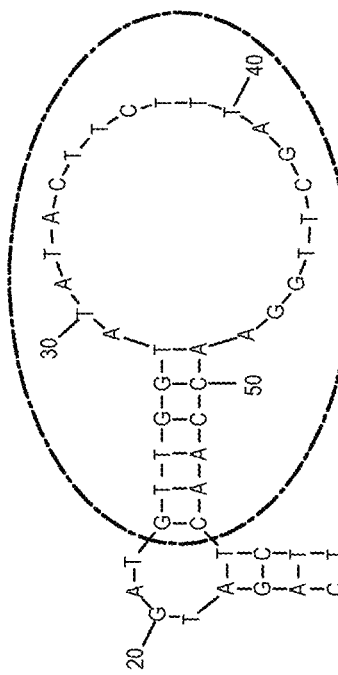
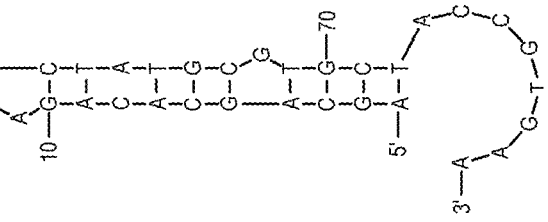
Structure of SQ7-1 (SEQ ID NO: 6)
Structure of SQ7 (SEQ ID NO: 4)

FIG. 8
Nuclei
Aptamer-Cy5
Control cells
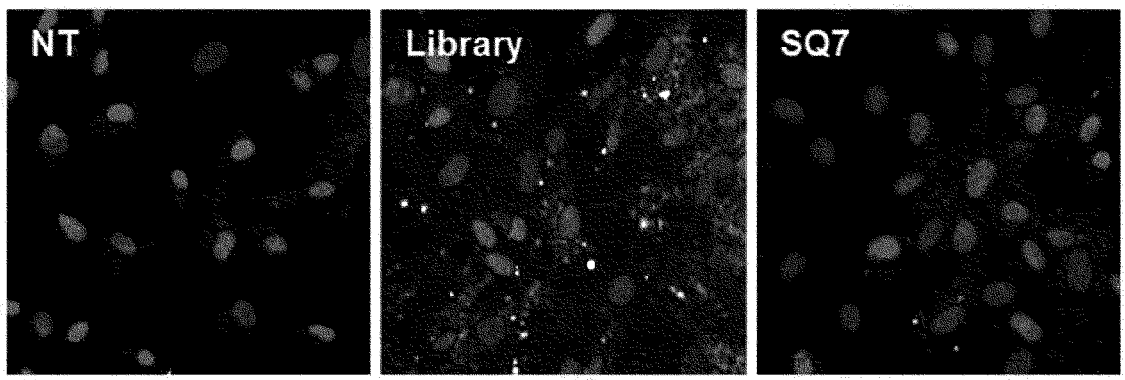
Target cells
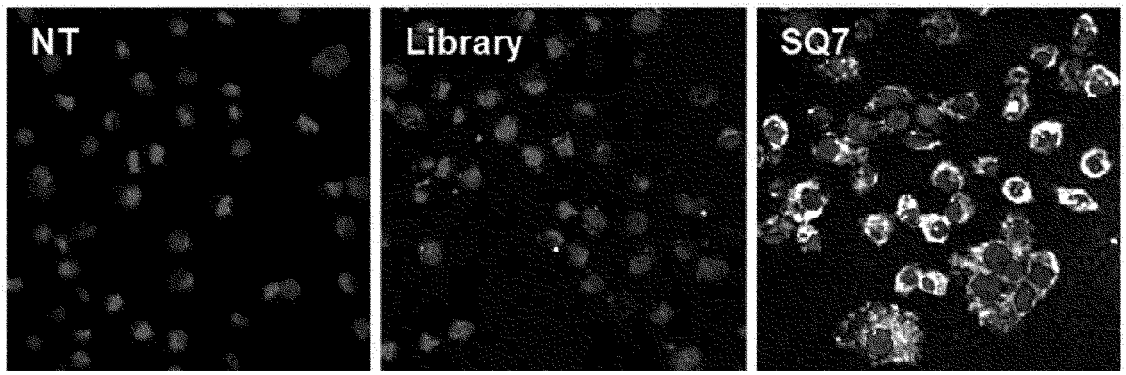

FIG. 10
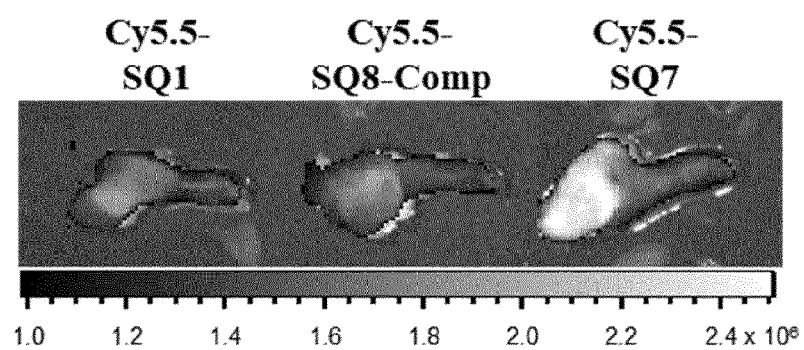
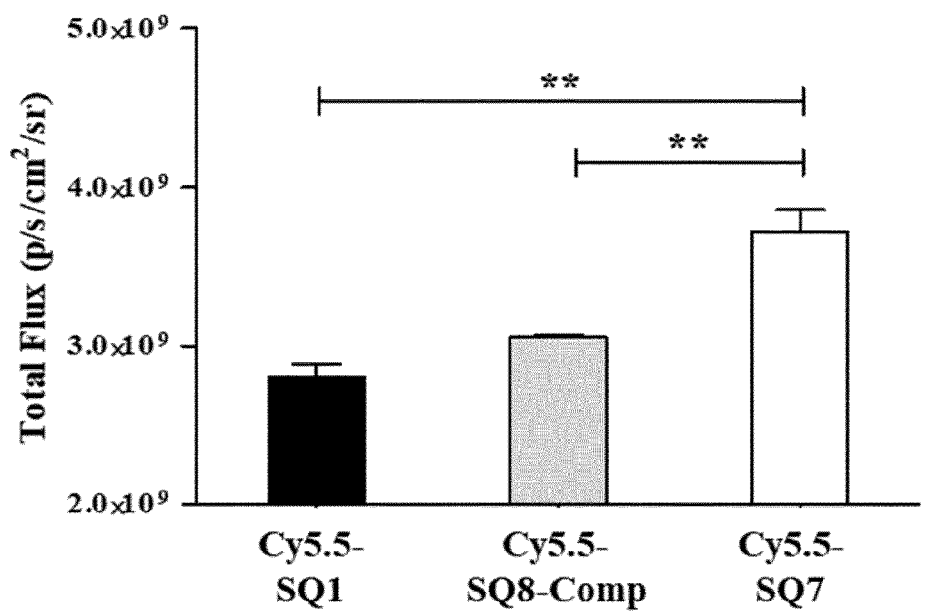

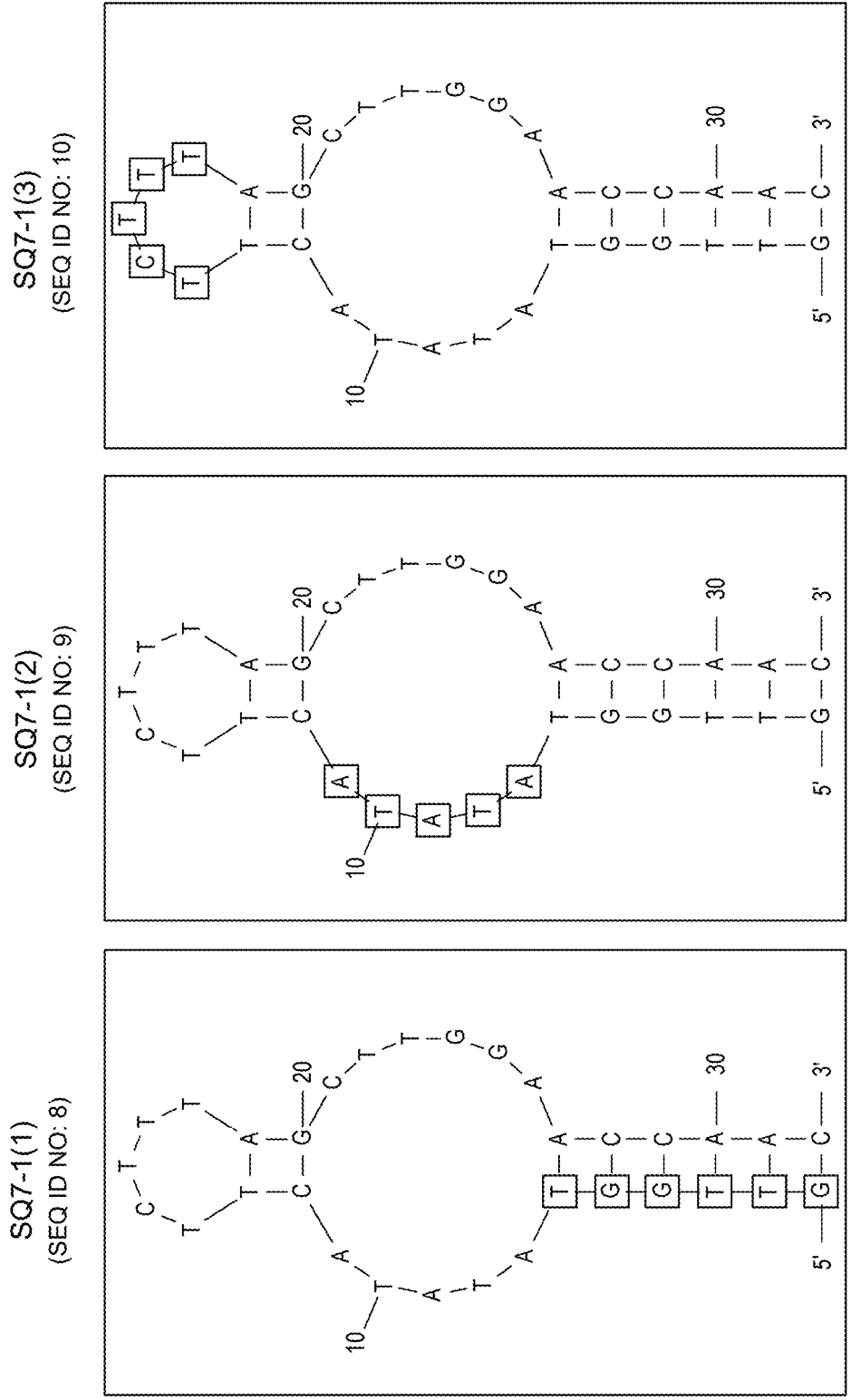

FIG. 12C
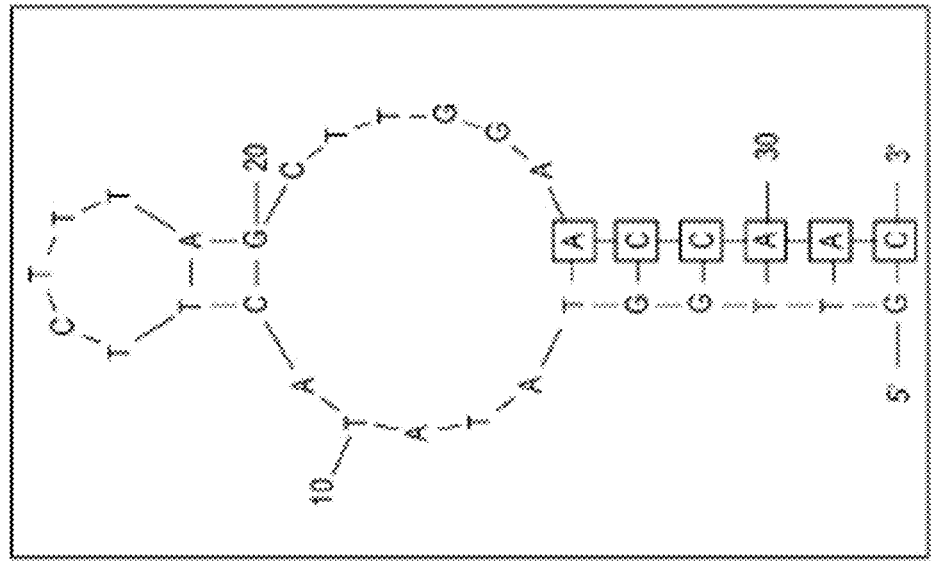
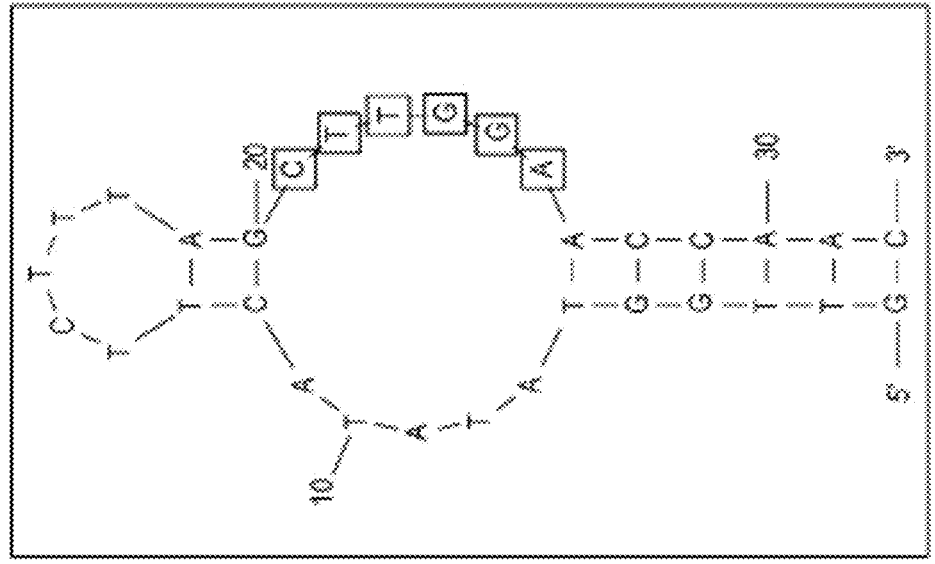

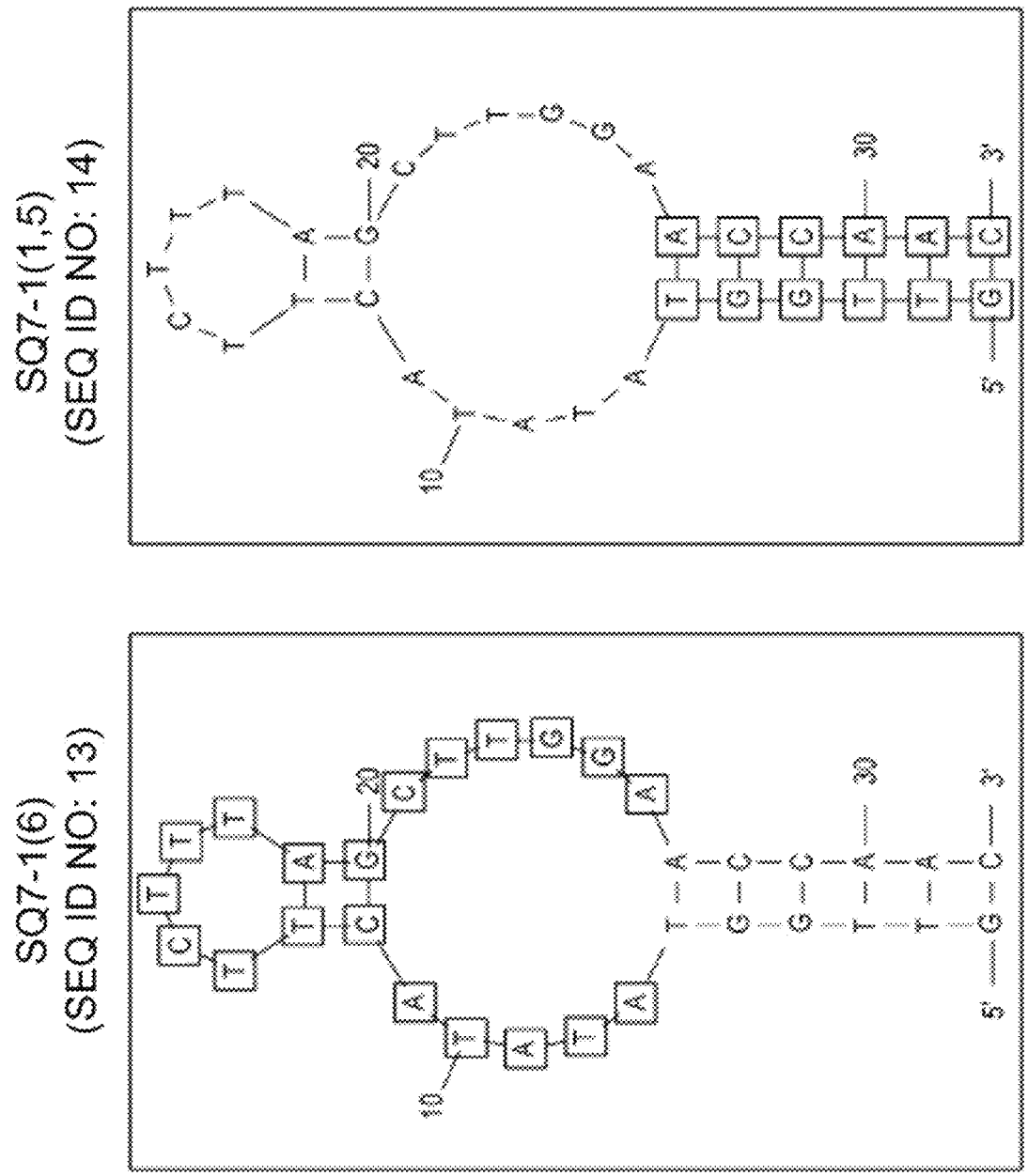

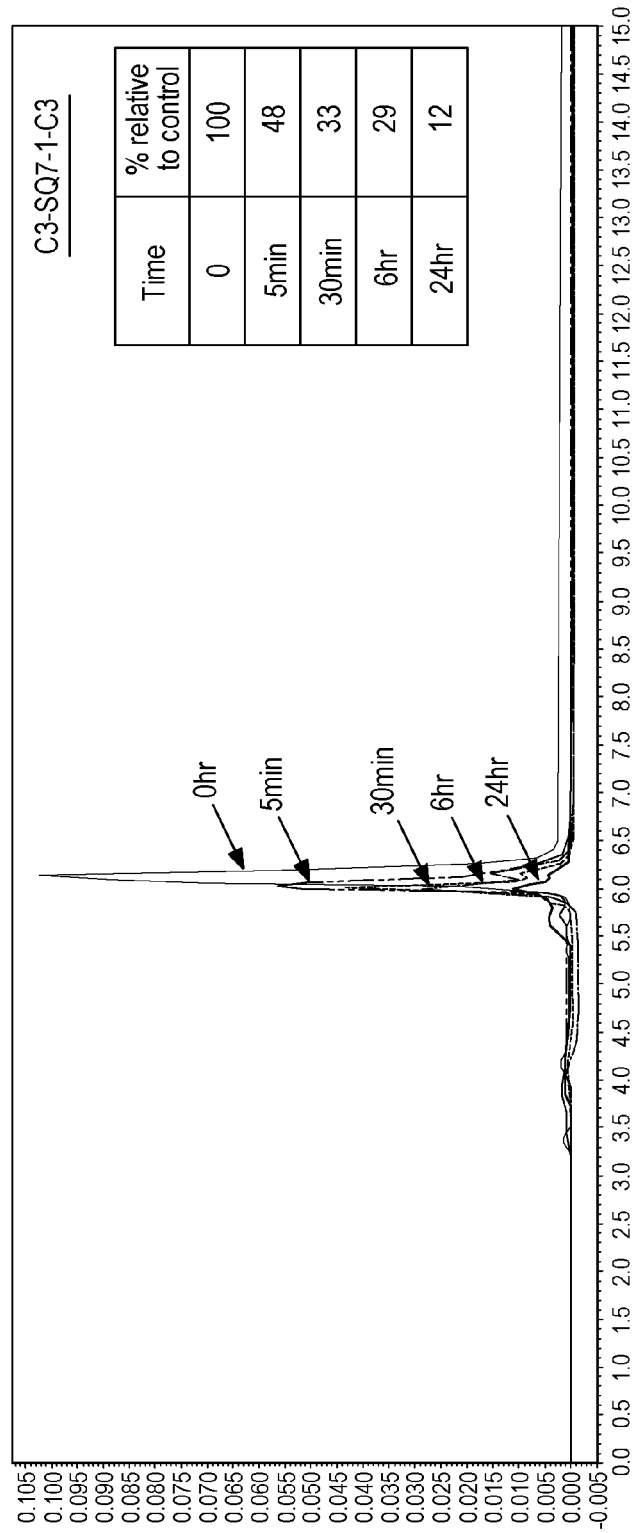

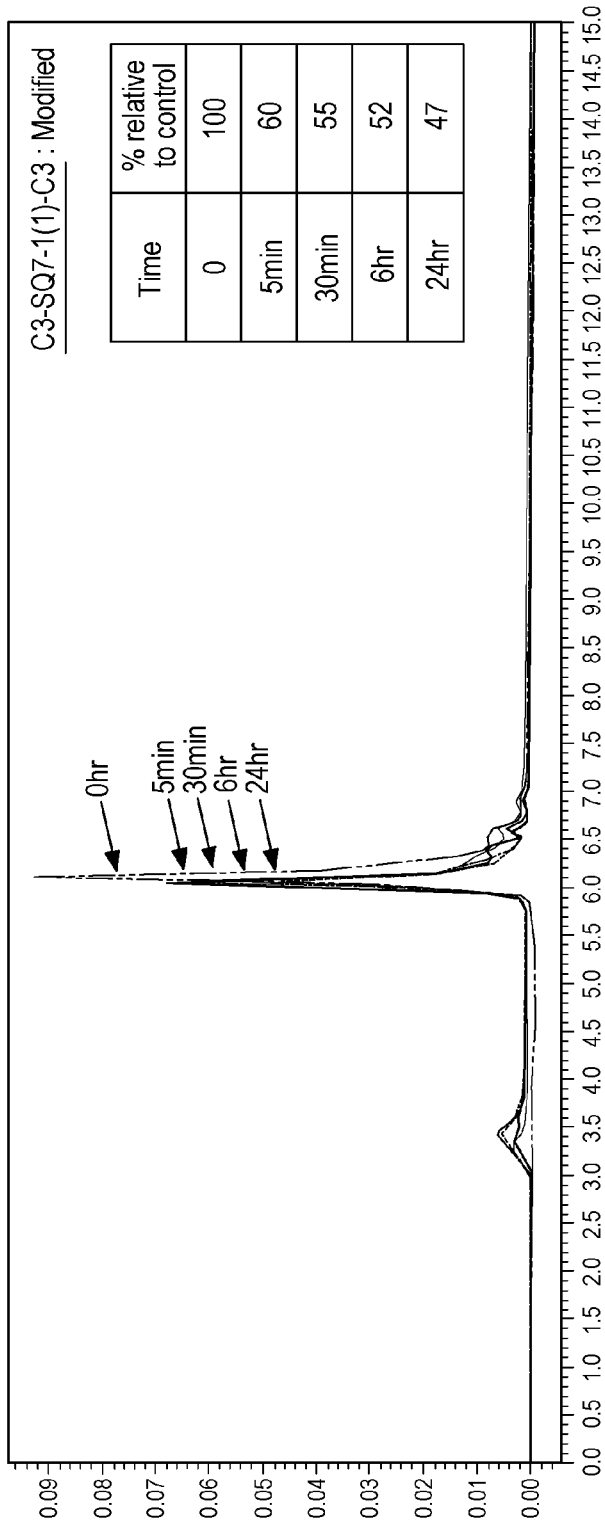

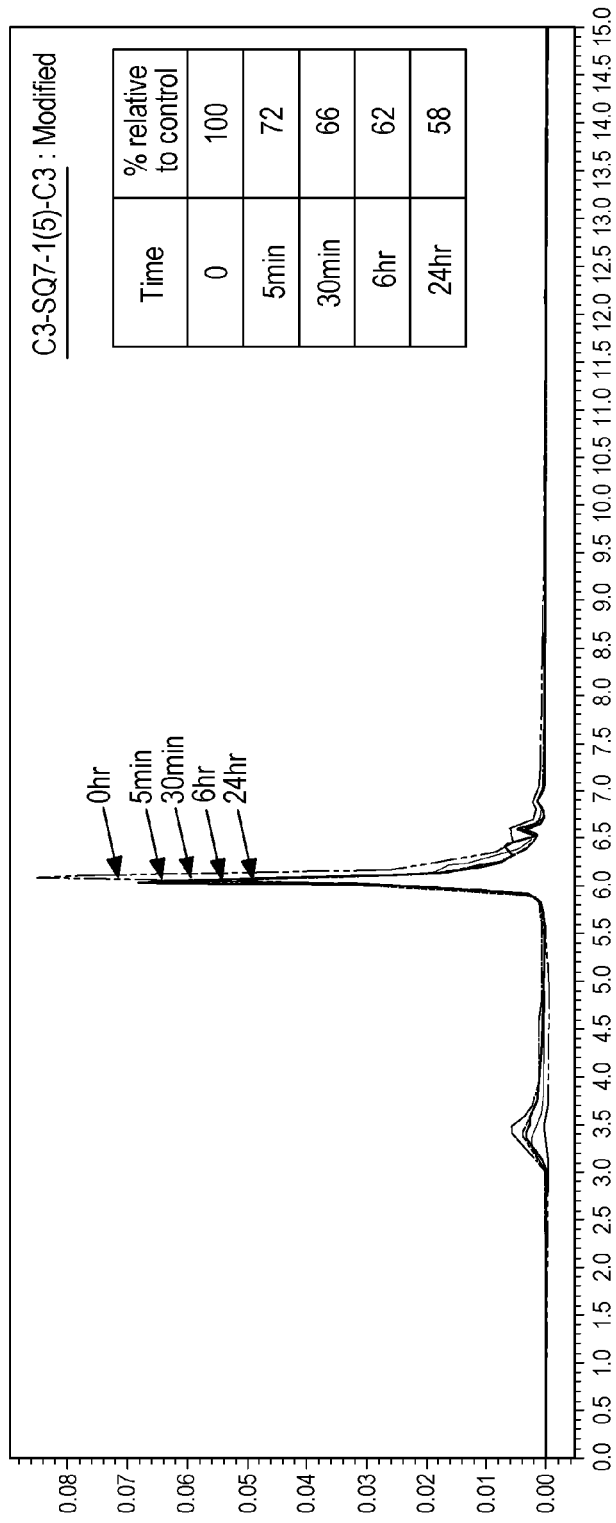

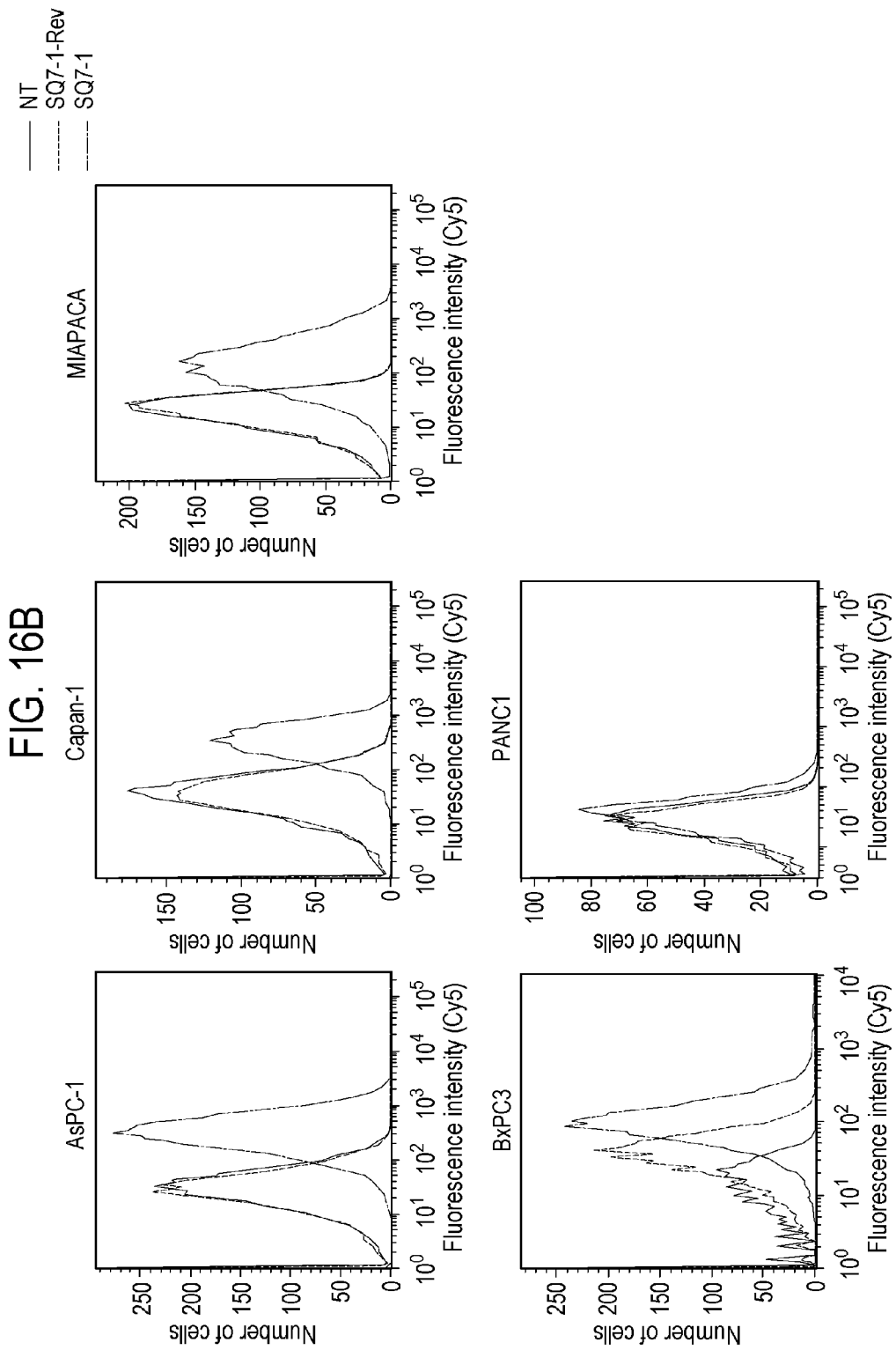

SEQUENCE LISTING

```
<160> NUMBER OF SEQ ID NOS: 17

<210> SEQ ID NO 1
<211> LENGTH: 76
<212> TYPE: DNA
<213> ORGANISM: Artificial Sequence
<220> FEATURE:
<223> OTHER INFORMATION: DNA library nucleotide format
<220> FEATURE:
<221> NAME/KEY: unsure
<222> LOCATION: (19)..(58)
<223> OTHER INFORMATION: DNA library randomized sequence from N19 to N58
<220> FEATURE:
<221> NAME/KEY: misc_feature
<222> LOCATION: (19)..(58)
<223> OTHER INFORMATION: n is a, c, g, or t
```

<400> SEQUENCE: 1
ataccagctt attcaattnn nnnnnnnnnn nnnnnnnnnn nnnnnnnnnn nnnnnnnnag    60
atagtaagtg caatct                                                    76

<210> SEQ ID NO 2
<211> LENGTH: 18
<212> TYPE: DNA
<213> ORGANISM: Artificial Sequence
<220> FEATURE:
<223> OTHER INFORMATION: DNA library primer forward
<220> FEATURE:
<221> NAME/KEY: 5'clip
<222> LOCATION: (1)..(1)
<223> OTHER INFORMATION: Cy5 attached to 5'

<400> SEQUENCE: 2
ataccagctt attcaatt                                                  18

<210> SEQ ID NO 3
<211> LENGTH: 18
<212> TYPE: DNA
<213> ORGANISM: Artificial Sequence
<220> FEATURE:
<223> OTHER INFORMATION: DNA library primer reverse
<220> FEATURE:
<221> NAME/KEY: 5'clip
<222> LOCATION: (1)..(1)
<223> OTHER INFORMATION: Biotin attached to 5'

<400> SEQUENCE: 3
agattgcact tactatct                                                  18

<210> SEQ ID NO 4
<211> LENGTH: 80
<212> TYPE: DNA
<213> ORGANISM: Artificial Sequence
<220> FEATURE:
<223> OTHER INFORMATION: DNA aptamer SQ7

<400> SEQUENCE: 4
agcagcacag aggtcagatg atgttggtat atacttcttt agcttggaac caactcttgc    60
cctatgcgtg ctaccgtgaa                                                80

<210> SEQ ID NO 5
<211> LENGTH: 80
<212> TYPE: DNA
<213> ORGANISM: Artificial Sequence
<220> FEATURE:
<223> OTHER INFORMATION: DNA aptamer SQ8-Comp

<400> SEQUENCE: 5
agcagcacag aggtcagatg gaacccgata aagaataagt acgacaaggt ggcgagagcc    60
cctatgcgtg ctaccgtgaa                                                80

<210> SEQ ID NO 6
<211> LENGTH: 32
<212> TYPE: DNA
<213> ORGANISM: Artificial Sequence
<220> FEATURE:
<223> OTHER INFORMATION: DNA aptamer SQ7-1

<400> SEQUENCE: 6
gttggtatat acttctttag cttggaacca ac                                  32

```
<210> SEQ ID NO 7
<211> LENGTH: 32
<212> TYPE: DNA
<213> ORGANISM: Artificial Sequence
<220> FEATURE:
<223> OTHER INFORMATION: DNA aptamer SQ7-1-Rev

<400> SEQUENCE: 7
caaccatata tgaagaaatc gaaccttggt tg                                    32

<210> SEQ ID NO 8
<211> LENGTH: 32
<212> TYPE: DNA
<213> ORGANISM: Artificial Sequence
<220> FEATURE:
<223> OTHER INFORMATION: internal 2'-O-methyl-modified aptamer SQ7-1(1);
      internal 2'-O-methyl-modified aptamers (from 1 to 6)
<220> FEATURE:
<221> NAME/KEY: modified_base
<222> LOCATION: (1)..(6)
<223> OTHER INFORMATION: 2'-O-methyl-modified bases from 1 to 6

<400> SEQUENCE: 8
guugguatat acttctttag cttggaacca ac                                    32

<210> SEQ ID NO 9
<211> LENGTH: 32
<212> TYPE: DNA
<213> ORGANISM: Artificial Sequence
<220> FEATURE:
<223> OTHER INFORMATION: internal 2'-O-methyl-modified aptamer SQ7-1(2);
      internal 2'-O-methyl-modified aptamers (from 7 to 11)
<220> FEATURE:
<221> NAME/KEY: modified_base
<222> LOCATION: (7)..(11)
<223> OTHER INFORMATION: 2'-O-methyl-modified bases from 7 to 11

<400> SEQUENCE: 9
gttggtauau acttctttag cttggaacca ac                                    32

<210> SEQ ID NO 10
<211> LENGTH: 32
<212> TYPE: DNA
<213> ORGANISM: Artificial Sequence
<220> FEATURE:
<223> OTHER INFORMATION: internal 2'-O-methyl-modified aptamer SQ7-1(3);
      internal 2'-O-methyl-modified aptamers (from 14 to 18)
<220> FEATURE:
<221> NAME/KEY: modified_base
<222> LOCATION: (14)..(18)
<223> OTHER INFORMATION: 2'-O-methyl-modified bases from 14 to 18

<400> SEQUENCE: 10
gttggtatat actucuuuag cttggaacca ac                                    32

<210> SEQ ID NO 11
<211> LENGTH: 32
<212> TYPE: DNA
<213> ORGANISM: Artificial Sequence
<220> FEATURE:
<223> OTHER INFORMATION: internal 2'-O-methyl-modified aptamer SQ7-1(4);
      internal 2'-O-methyl-modified aptamer (from 21 to 26)
<220> FEATURE:
<221> NAME/KEY: modified_base
<222> LOCATION: (21)..(26)
<223> OTHER INFORMATION: 2'-O-methyl-modified bases from 21 to 26

<400> SEQUENCE: 11
gttggtatat acttctttag cuuggaacca ac                                    32
```

```
<210> SEQ ID NO 12
<211> LENGTH: 32
<212> TYPE: DNA
<213> ORGANISM: Artificial Sequence
<220> FEATURE:
<223> OTHER INFORMATION: internal 2'-O-methyl-modified aptamer SQ7-1(5);
      internal 2'-O-methyl-modified aptamers (from 27 to 32)
<220> FEATURE:
<221> NAME/KEY: modified_base
<222> LOCATION: (27)..(32)
<223> OTHER INFORMATION: 2'-O-methyl-modified bases from 27 to 32

<400> SEQUENCE: 12
gttggtatat acttctttag cttggaacca ac                                      32

<210> SEQ ID NO 13
<211> LENGTH: 32
<212> TYPE: DNA
<213> ORGANISM: Artificial Sequence
<220> FEATURE:
<223> OTHER INFORMATION: internal 2'-O-methyl-modified aptamer SQ7-1(6);
      internal 2'-O-methyl-modified aptamers (from 7 to 26)
<220> FEATURE:
<221> NAME/KEY: modified_base
<222> LOCATION: (7)..(26)
<223> OTHER INFORMATION: 2'-O-methyl-modified bases from 7 to 26

<400> SEQUENCE: 13
gttggtauau acuucuuuag cuuggaacca ac                                      32

<210> SEQ ID NO 14
<211> LENGTH: 32
<212> TYPE: DNA
<213> ORGANISM: Artificial Sequence
<220> FEATURE:
<223> OTHER INFORMATION: internal 2'-O-methyl-modified aptamer
      SQ7-1(1,5); internal 2'-O-methyl-modified aptamers (from 1 to 6,
      from 27 to 32)
<220> FEATURE:
<221> NAME/KEY: modified_base
<222> LOCATION: (1)..(6)
<223> OTHER INFORMATION: 2'-O-methyl-modified bases from 1 to 6
<220> FEATURE:
<221> NAME/KEY: modified_base
<222> LOCATION: (27)..(32)
<223> OTHER INFORMATION: 2'-O-methyl-modified bases from 27 to 32

<400> SEQUENCE: 14
guugguatat acttctttag cttggaacca ac                                      32

<210> SEQ ID NO 15
<211> LENGTH: 79
<212> TYPE: DNA
<213> ORGANISM: Artificial Sequence
<220> FEATURE:
<223> OTHER INFORMATION: DNA aptamer SQ7a

<400> SEQUENCE: 15
agcagcacag aggtcagatg atgttggtat atacttcttt agcttggaac caactcttct        60
cctatgcgtg ctaccgtga                                                    79

<210> SEQ ID NO 16
<211> LENGTH: 80
<212> TYPE: DNA
<213> ORGANISM: Artificial Sequence
<220> FEATURE:
<223> OTHER INFORMATION: DNA aptamer SQ7b
```

```
<400> SEQUENCE: 16
agcaacacag aggtcagatg atgttggtat atacttcttt agcttggaac ccactcttgt    60
cctatgcgtg ctaccgtgaa                                                80

<210> SEQ ID NO 17
<211> LENGTH: 80
<212> TYPE: DNA
<213> ORGANISM: Artificial Sequence
<220> FEATURE:
<223> OTHER INFORMATION: DNA aptamer SQ1

<400> SEQUENCE: 17
agcagcacag aggtcagatg cttgggctat ctcttattca tgctgttcca ccgctctcgg    60
cctatgcgtg ctaccgtgaa                                                80
```

DNA APTAMERS FOR PANCREATIC CANCER DETECTION

CROSS REFERENCE TO RELATED APPLICATIONS

This application is a National Stage of International Application No. PCT/KR2019/009956 filed Aug. 8, 2019, claiming priority based on Korean Patent Application No. 10-2018-0167948 filed Dec. 21, 2018, the entire disclosures of which are incorporated herein by reference.

INCORPORATION BY REFERENCE OF SEQUENCE LISTING

The content of the sequence listing, file name: Q265187_Sequence Listing as filed.txt; size 5,798 bytes; and date of creation of Jun. 21, 2021, filed Jun. 21, 2021, is incorporated herein by reference in its entirety.

TECHNICAL FIELD

The present disclosure relates to novel DNA aptamers. In particular, the present disclosure relates to DNA aptamers selected from a cancer DNA library using Cell-SELEX to bind specifically to cancer cells. The present disclosure also relates to compositions comprising a novel DNA aptamer for targeting cancer tissues, diagnosing a cancer, or treating a cancer. The present disclosure is based on a study conducted both as an original research project of the National Cancer Center (NCC) and part of the TIPS program (Tech Incubator Program for Startup) of the Ministry of SMEs and Startups.

[Project No.: NCC-1210080, Title: Identification of pancreatic cancer-specific metastasis factors using Cell-SELEX]

[Project No.: NCC-1410270, Title: Development of innovative anticancer agents through establishment of aptamer-antibody conjugate platform]

[Project No.: S2562351, Title: Development of therapeutic agents for pancreatic cancer using aptamer-antibody-drug conjugates]

BACKGROUND

Aptamers refer to single-stranded DNA or RNA oligonucleotides that have unique three dimensional structures and specifically bind to target molecules in a manner similar to antibodies. In general, aptamers have high affinity in concentrations as low as nanomoles to picomoles.

Aptamers are commonly compared to antibodies because of their target-specific binding properties. Compared with antibodies, aptamers are easily produced by chemical synthesis without the need to employ biological processes using cells or animals, relatively stable at high temperatures, and superior in accessibility to targets owing to their small sizes. In addition, aptamers have advantages over antibodies in terms of potential as therapeutic agents in that they can be easily modified in the course of chemical synthesis and are not immunogenic and nontoxic. However, aptamers have the drawback that they have a short half-life as they are degraded by nucleases in vivo. This drawback can be overcome by various chemical modifications.

Cancer needs to be discovered and treated in an early phase. Particularly, pancreatic cancer is a carcinoma showing the worst prognosis, with its 1-year mortality rate being the highest among all carcinomas. The 2-year survival rate for pancreatic cancer is about 10%, and the 5-year survival rate is only 8% or lower. Over the past two decades, 5-year survival rates in almost all cancers have greatly increased, but pancreatic cancer has given very dismal results, increasing from 3% reported in 1997 to only about 8% in 2016.

Actually, only 20% or so of pancreatic cancer patients are deemed to be operable, and even in such cases, a high survival rate of 90% or greater after operation can be expected only when the tumor size is 1 cm or less with no lymph node metastasis or distant metastasis. However, most patients are already inoperable at the time of diagnosis. When the tumor is inoperable, patients typically rely on chemotherapies or radiation therapies. However, since clearly standardized therapies are not currently available, early detection of pancreatic cancer is important in improving the survival rates.

Pancreatic cancer has almost no early symptoms, and by the time a patient can recognize symptoms, the cancer has already progressed to an advanced stage in most cases. Consequently, early diagnosis of pancreatic cancer is very difficult. Currently, practically no early detection markers are available for pancreatic cancer.

Early pancreatic cancer is generally defined as tumors that have a size of less than 2 cm and that are confined to the pancreas with no infiltrations or lymph node metastases. However, even when the size of pancreatic cancer is less than 2 cm, the threshold for early pancreatic cancer, metastasis has been found in as many as 50% of such cases. Even in stage II, which is classified as early pancreatic cancer when staging pancreatic cancer based on the size of tumor, lymph node metastasis, and distant metastasis, it is common to find infiltrations in regions connecting to the superior mesenteric vein or portal vein, as well as early metastasis by a small number of cells. In such cases, the tumor is not resectable. In cases where the tumor has been operated considering that distant metastasis was not found on the scan and tumor was determined to be confined to the pancreas, it is not uncommon that distant metastasis is found shortly after the operation. In such a case, risk of recurrence is very high even after a surgery, and median survival is only 6~12 months since there are no anticancer agents with outstanding efficacy. Given the foregoing, there is a need for detecting early pancreatic cancer that has not advanced to substantial distant metastasis or early metastasis by a small number of cells, at least for the purpose of early surgical resection, the only curative treatment of pancreatic cancer.

In developing probes specific to cell surface proteins, extracellular domains of a cell surface protein can be isolated and purified in the form of a recombinant protein and then used as an antigen to develop antibodies or for selection of aptamers. The screening process for selection of aptamers is generally called SELEX (systematic evolution of ligands by exponential enrichment) technique. This technique typically uses isolated recombinant proteins. However, the three-dimensional structure of cell surface proteins is likely to be altered in the course of isolation, which may lead to a situation where the selected aptamers cannot actually bind to the target protein on the cell surface if the three-dimensional structure of the protein is critical for the binding with the target protein.

Such limitations may be overcome by using the Cell-SELEX method, which involves selecting aptamers cell membrane specifically using living cells unlike the conventional SELEX technique.

In the present disclosure, DNA aptamers having a high binding affinity to pancreatic cancer were selected using the Cell-SELEX method on pancreatic cancer cells, followed by further research on the selected aptamers to improve cell and tissue targeting efficiency and serum stability. It has been found that the selected aptamers can specifically bind to various kinds of cancer including, in addition to pancreatic cancer, colon cancer, liver cancer, lung cancer, brain tumor, oral cavity cancer, ovary cancer, and breast cancer.

Prior Art Literature (Patent literature 1) KR 10-1458947
(Patent literature 2) KR 10-1250557

SUMMARY

It is an object of the present disclosure to provide novel DNA aptamers. In particular, the novel DNA aptamers are DNA aptamers that show cancer-specific binding.

It is another object of the present disclosure to provide a method for diagnosing or treating a cancer using DNA aptamers that show cancer-specific binding.

The present disclosure aims to develop aptamers useful in probing cancer cells. Aptamers that specifically bind to cell membranes of pancreatic cancer have been selected using the Cell-SELEX technique. Specifically, in the present disclosure, aptamers that specifically bind to pancreatic cancer cells have been selected using CMLu-1 cells isolated from metastasized pancreatic cancer tissue as target cells and normal pancreas tissue cell HPNE as control.

In one aspect, the present disclosure provides a DNA aptamer comprising the nucleotide sequence of SEQ ID NO: 6. In another aspect, the present disclosure provides a DNA aptamer comprising a nucleotide sequence having at least 90% or 95% homology to the nucleotide sequence of SEQ ID NO: 6. In one aspect of the present disclosure, the DNA aptamer may show cancer-specific binding. In one aspect of the present disclosure, the DNA aptamer may consist of the nucleotide sequence of SEQ ID NO: 6.

In another aspect, the present disclosure provides a DNA aptamer consisting of a nucleotide sequence having at least 90% or 95% homology to the nucleotide sequence of SEQ ID NO: 4. In one aspect of the present disclosure, the DNA aptamer may consist of the nucleotide sequence of SEQ ID NO: 4.

As used herein, "a nucleotide sequence having at least 90% homology" refers to a nucleotide sequence that comprises addition, deletion, or substitution of one to several nucleotides to have 90% or greater, but less than 100%, identity in nucleotide sequence relative to a reference sequence and shows similar cancer-specific binding.

In one aspect of the present disclosure, having at least 90% homology to the nucleotide sequence of SEQ ID NO: 4 may refer to having a nucleotide sequence that differs from the nucleotide sequence of SEQ ID NO: 4 in a region of SEQ ID NO: 4 other than the region corresponding to the nucleotide sequence of SEQ ID NO: 6.

As used herein, the term "DNA aptamers" refers to short, single-stranded oligonucleotides that bind to corresponding targets with high affinity and specificity and have unique three-dimensional structures. Through a process of iterative in vitro selection and enrichment, DNA molecules that specifically bind to a specific target, i.e., DNA aptamers, can be selected from a DNA aptamer library.

In an experimental example of the present disclosure, aptamers of a DNA pool enriched through the Cell-SELEX process were clustered on the basis of their sequence similarity into 11 aptamer families (SQ1 to SQ11). Among the families, SQ7 has been identified as a group having high binding affinity to CMLu-1, pancreatic cancer-derived metastatic cancer cells, and the SQ7 family included aptamers which show high sequence homology to each other and differ only in some nucleotides (SQ7a and SQ7b aptamers in Table 3).

In addition, using as template the SQ7 (SEQ ID NO: 4) aptamer (80-mer), which specifically binds to pancreatic cancer tissue derived cells, a truncated aptamer (32-mer) was prepared in order to enhance synthesis yields and reduce costs of synthesis. Specifically, the SQ7-1 aptamer (SEQ ID NO: 6) was prepared, which reduces the size of aptamer by greater than one half while retaining the binding affinity to CMLu-1 target cells. The inventors of the present disclosure concluded that the SQ7-1 aptamer is a region of the SQ7 aptamer sequence which is critical for its ability to target cancer cells and cancer tissue, and based thereon, conducted further experiments.

In one aspect of the present disclosure, provided are modified DNA aptamers wherein modifications have been introduced into the DNA aptamers of the present disclosure such that they have resistance to DNase, and the modifications may be found in at least 10% of the nucleotides in SEQ ID NO: 6. In addition, the modified DNA aptamer may have a nucleotide sequence of SEQ ID NOs: 8, 12, or 14.

In one aspect of the present disclosure, the modifications introduced to impart DNase resistance may be substitution of —OH group at 2' carbon of a sugar moiety in one or more nucleotides with -Me (methyl), —OMe, —NH$_2$, —F (fluorine), —O-2-methoxyethyl —O-propyl, —O-2-methylthioethyl, —O-3-aminopropyl, —O-3-dimethylaminopropyl, —O—N-methylacetamido or —O-dimethylamidoxyethyl.

In a working example of the present disclosure, based on the SQ7-1 aptamer as the template, internal 2'-O-methyl-modified aptamers were prepared by modifying different regions in the secondary structure of the SQ7-1 aptamer, and the serum half-lives of the modified aptamers were determined to investigate their serum stability. The results showed that some modified aptamers exhibit 90-fold or greater increases in serum half-life relative to the SQ7-1 aptamer.

The target cells used for Cell-SELEX in the working examples of the present disclosure were CMLu-1 cells, which were obtained from metastatic pancreatic cancer tissue through an orthotopic graft experiment. Accordingly, the present disclosure may be useful particularly for the diagnosis of pancreatic cancer.

The present disclosure provides a composition for targeting cancer tissues, comprising a DNA aptamer described above. In one aspect of the present disclosure, the composition comprising a DNA aptamer may further comprise, in addition to the above component, an active ingredient having the same or similar function, or a component that stabilizes the formulation of the composition or enhances the stability of the aptamer. In one aspect of the present disclosure, the composition may be a pharmaceutical composition.

In addition, the present disclosure provides a composition for diagnosing a cancer comprising an aptamer according to an aspect of the present disclosure.

In one aspect of the present disclosure, a DNA aptamer can be used in combination with an effector moiety.

In one aspect of the present disclosure, the effector moiety may be a cytotoxic agent, an immunosuppressive agent, an imaging agent (e.g., a fluorescent moiety or chelator), a nanomaterial or a toxin polypeptide. The cytotoxic agent may be a chemotherapeutic agent.

In one aspect, the present disclosure relates to composition for treating a cancer, comprising a novel DNA aptamer according to an aspect of the present disclosure and an anticancer agent conjugated with the DNA aptamer.

In one aspect of the present disclosure, the cancer may be pancreatic cancer, colon cancer, liver cancer, lung cancer, brain tumor, oral cavity cancer, ovary cancer, or breast cancer, but is not limited thereto.

In one aspect of the present disclosure, the anticancer agent may be one or more selected from the group consisting of MMAE (monomethyl auristatin E), MMAF (monomethyl auristatin F), calicheamicin, mertansine (DM1), ravtansine (DM4), tesirine (SCX), doxorubicin, cisplatin, SN-38, duocarmycin, and (yrrolobenzodiazepine (PBD), but is not limited thereto.

In one aspect of the present disclosure, the DNA aptamer may be conjugated with a polyethylene glycol (PEG) or its derivative, a diacylglycerol (DAG) or its derivative, an antibody, a dendrimer, or a zwitter ion-containing biocompatible polymer (e.g., a phosphorylcholine-containing polymer).

In one aspect of the present disclosure, the composition may further contain a physiologically acceptable excipient, carrier, or additive, which may include, but is not limited to, starch, gelatinized starch, microcrystalline cellulose, lactose, povidone, colloidal silicon dioxide, calcium hydrogen phosphate, lactose, mannitol, taffy, gum arabic, pregelatinized starch, corn starch, cellulose powder, hydroxypropyl cellulose, Opadry, sodium starch glycolate, carnauba wax, synthetic aluminum silicate, stearic acid, magnesium stearate, aluminum stearate, calcium stearate, white sugar, dextrose, sorbitol, and talc.

In one aspect of the present disclosure, the composition may be administered to subjects in a variety of forms according to the selected route of administration as understood by a person of ordinary skill in the relevant technical fields. For example, a composition of the present disclosure may be administered by topical, enteral, or parenteral application. Topical application includes, but is not limited to, application to epidermis, inhalation, enema, eye drop, ear drop, and mucosal application. Enteral application includes oral administration, rectal administration, vaginal administration, and gastric feeding tube. Parenteral administration includes, but is not limited to, intravenous, intra-arterial, intracapsular, intraorbital, intracardiac, intracutaneous, transtracheal, subcuticular, intra-articular, subcapsular, subarachnoid, intramedullary, epidural, intrasternal, intraperitoneal, subcutaneous, intramuscular, transepithelial, intranasal, intrapulmonary, intrathecal, rectal, and topical administration.

In addition, in one aspect of the present disclosure, the composition may be formulated into any forms suitable for the selected route of administration. For formulation purposes, the composition may be prepared using diluents or excipients including, but not limited to, a filler, an extender, a binder, a wetting agent, a disintegrant, a surfactant, and the like.

In one aspect of the present disclosure, the composition may contain a DNA aptamer according to an aspect of the present disclosure in an amount determined by a person of ordinary skill in the art to be effective considering the route of administration as well as the weight, age, sex, health condition, diet, time of intake, and excretion rate etc. of the subject in need of administration.

The DNA aptamers of the present disclosure selected and optimized for high binding affinity to cancer cells can be effectively used for the diagnosis and treatment of cancer as they have enhanced targeting efficiencies for target cells and tissues as well as high serum stability.

(A) and (B) of FIG. 3 schematically illustrate the process of screening aptamers through Cell-SELEX technique using metastatic pancreatic cancer cells in the present disclosure.

Figure 4:
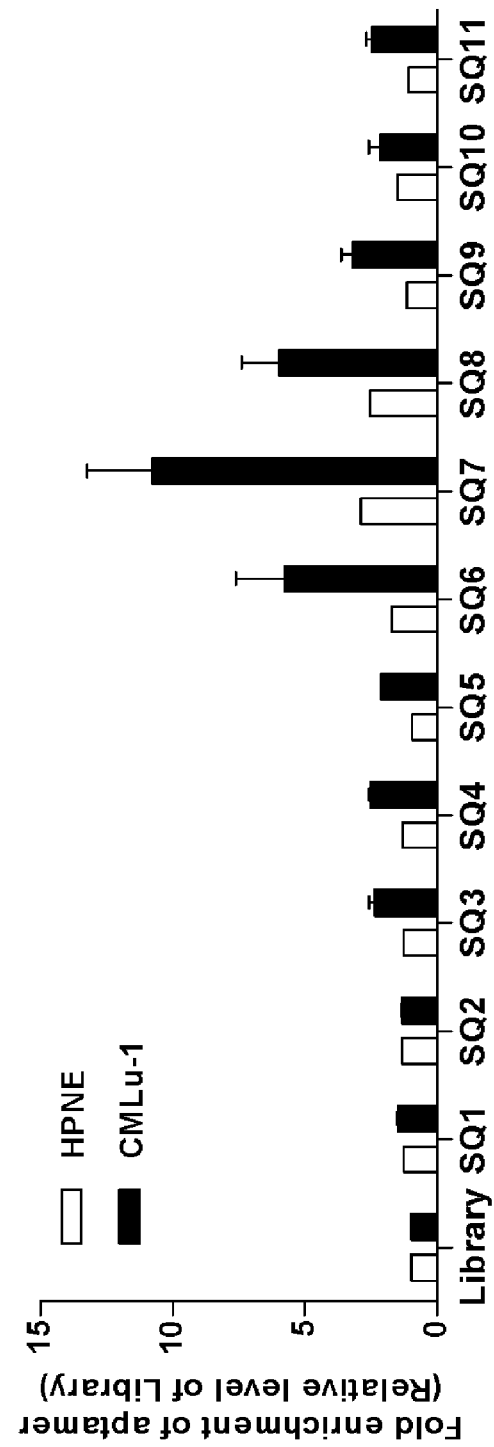

FIG. 4 shows the results from the determination of cell binding affinity of individual Cy5-labeled aptamer candidates obtained by screening aptamers through Cell-SELEX technique using metastatic pancreatic cancer cells in the present disclosure.

Figure 5:
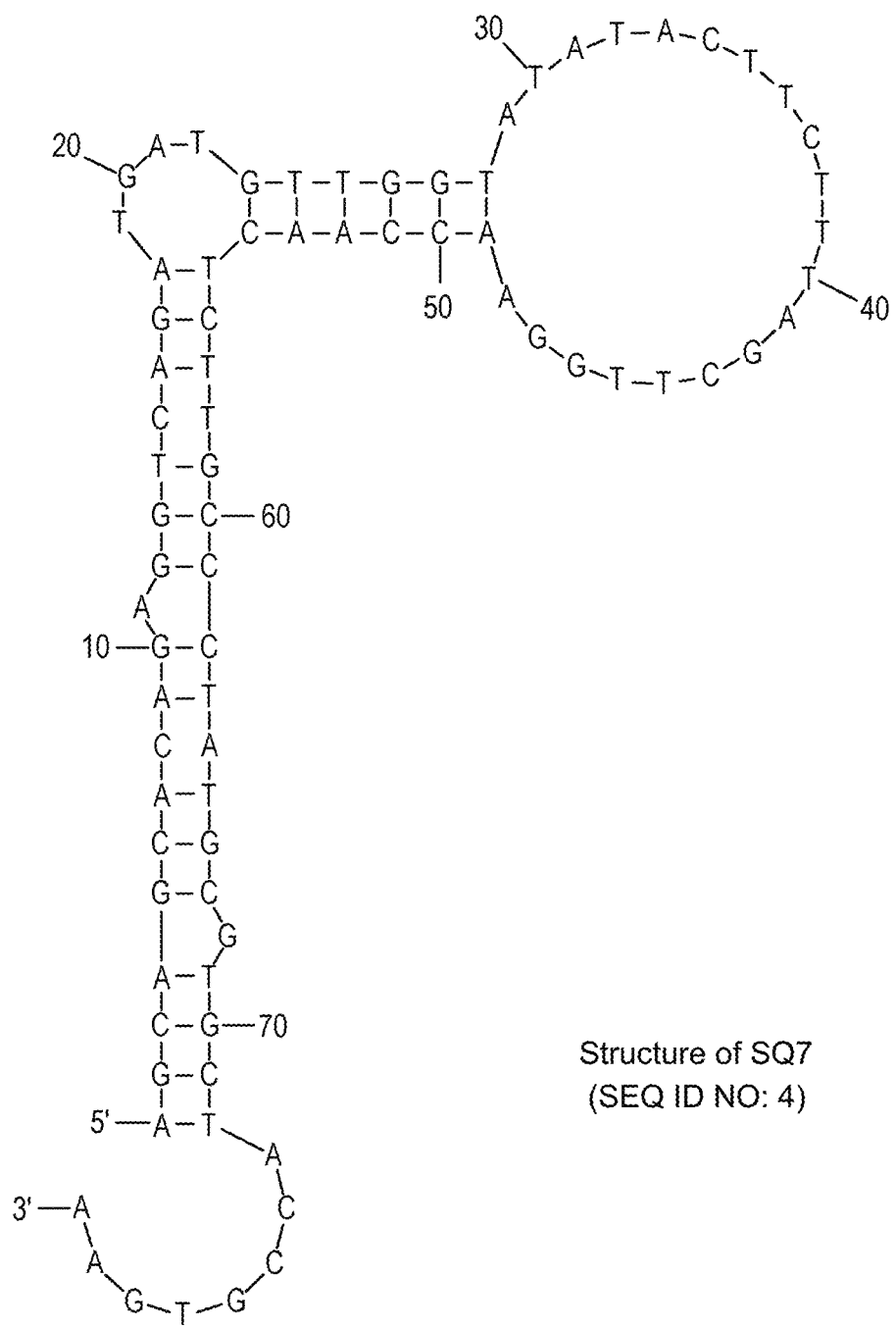

FIG. 5 depicts the secondary structure determined for the SQ7 aptamer obtained by screening aptamers through Cell-SELEX technique using metastatic pancreatic cancer cells in the present disclosure.

FIG. 6a shows the results from the determination of target cell binding affinity of the SQ7 aptamer of the present disclosure using a flow cytometer (FACS). Specifically, target cell binding was determined for the SQ7 aptamer and, as controls, no-treatment control (NT), the DNA pool library, and the SQ8-Comp aptamer.

FIG. 6b shows the results from the determination of target cell binding affinity of the SQ7-1 aptamer of the present disclosure using a flow cytometer (FACS). Specifically, target cell binding was determined for the SQ7 aptamer and SQ7-1 aptamer, and, as controls, no-treatment control (NT), the DNA pool library, and the SQ8-Comp aptamer.

FIG. 7 depicts the secondary structure of the SQ7-1 aptamer, which was prepared based on the SQ7 aptamer of the present disclosure.

FIG. 8 shows targeting profile of the SQ7 aptamer of the present disclosure for target cells determined with confocal microscopy. Gray ellipses represent nuclei, and the brightest looking, white areas represent aptamers that are bound to cell surfaces or internalized into cells.

Figure 9:
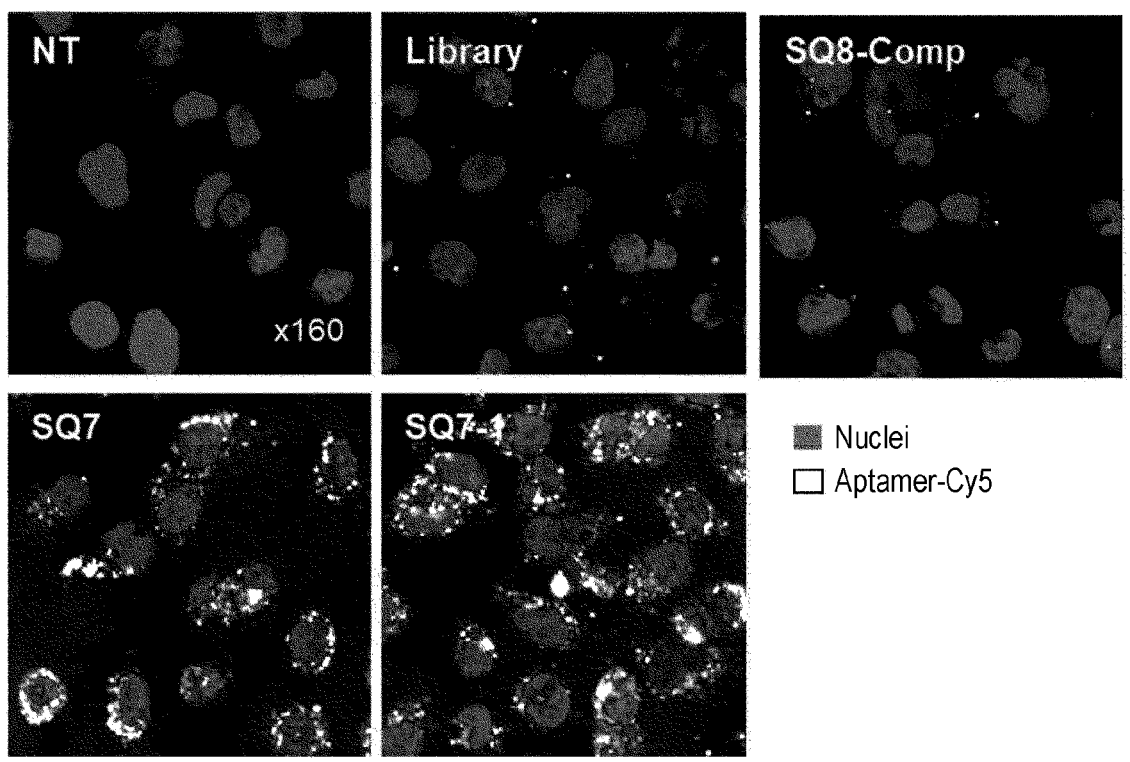

FIG. 9 shows targeting profile of the SQ7-1 aptamer of the present disclosure for target cells determined with confocal microscopy. Gray ellipses represent nuclei, and the brightest looking, white areas represent aptamers that are bound to cell surfaces or internalized into cells.

FIG. 10 shows targeting profile of the SQ7 aptamer of the present disclosure for pancreatic cancer tissue determined with bioluminescence imaging in a xenograft mouse model for a human pancreatic cancer cell line.

Figure 11:
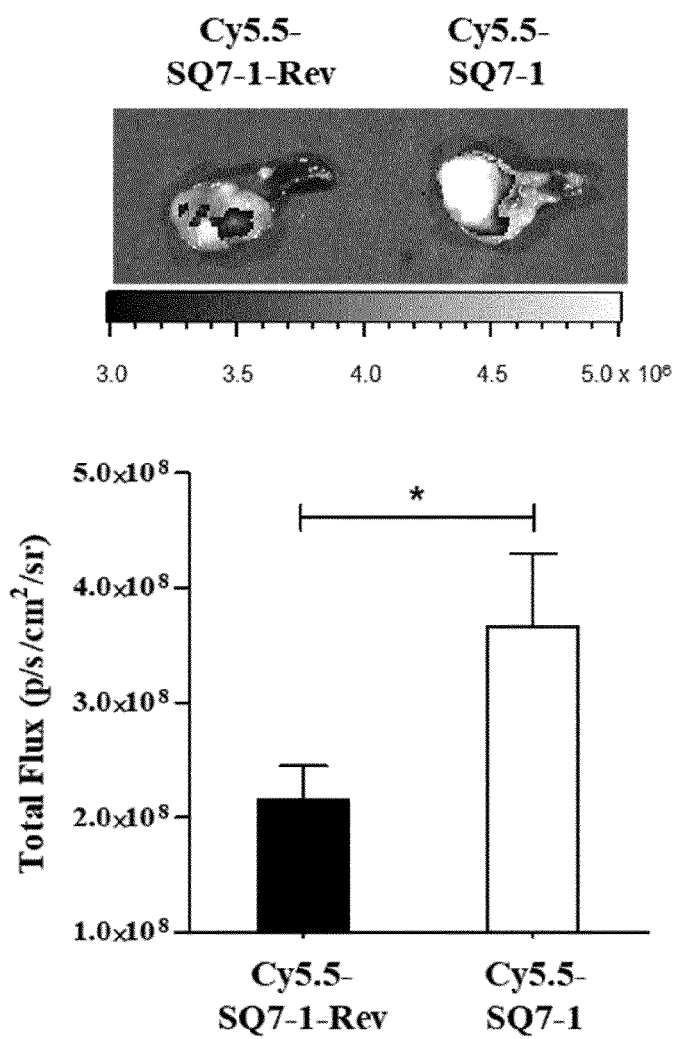

FIG. 11 shows targeting profile of the SQ7-1 aptamer of the present disclosure for pancreatic cancer tissue determined with bioluminescence imaging in a xenograft mouse model for a human pancreatic cancer cell line.

Figure 12A:
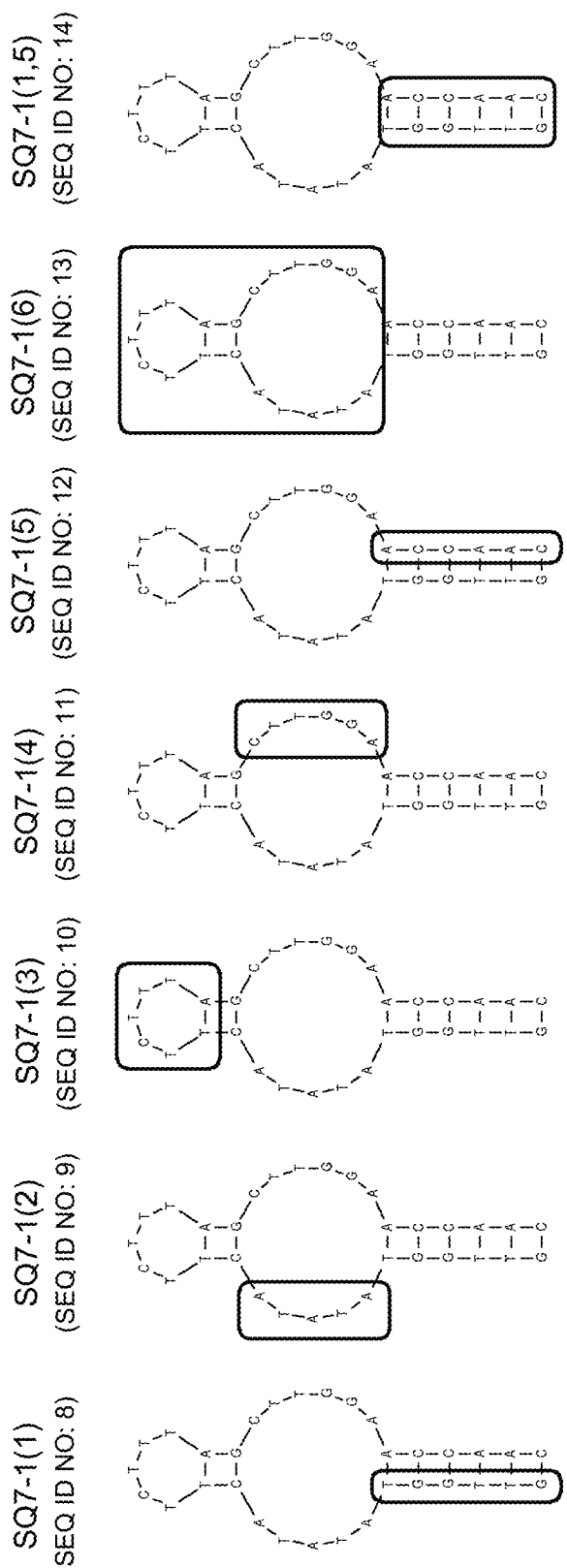
Figure 13D:
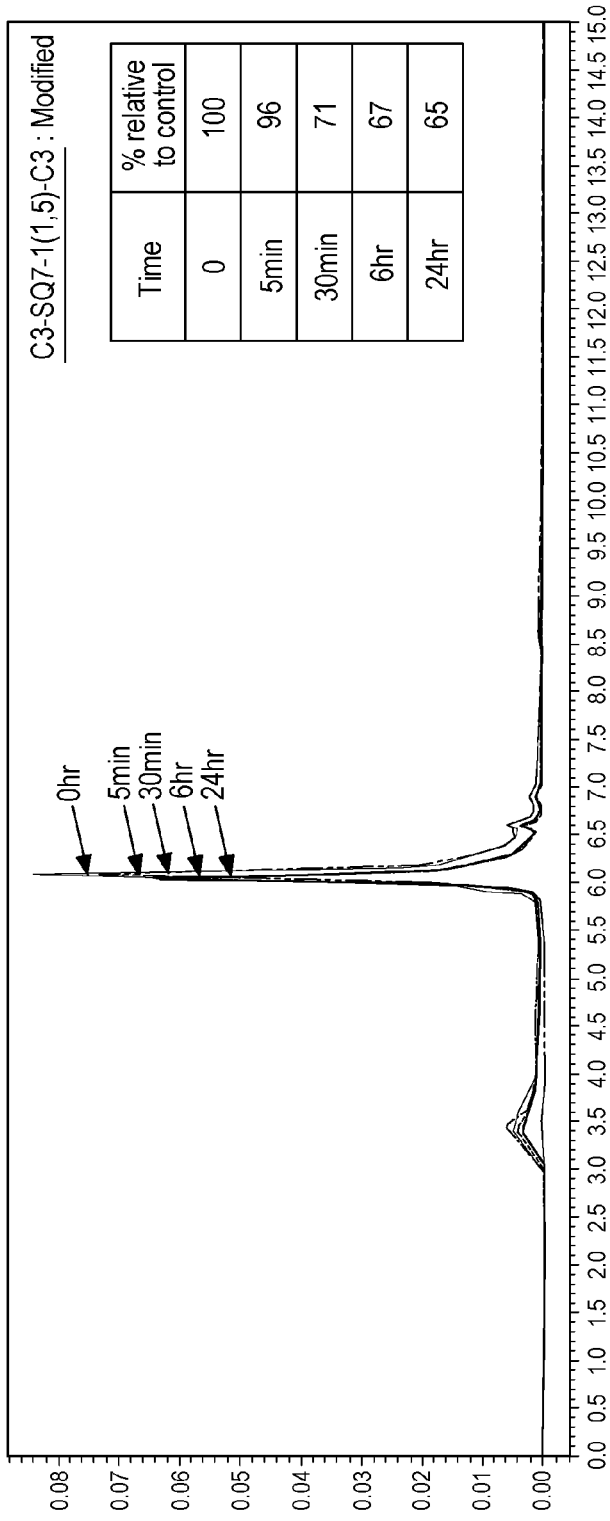

FIG. 12a to FIG. 12d depict the secondary structures and modified positions of the SQ7-1(1), SQ7-1(2), SQ7-1(3), SQ7-1(4), SQ7-1(5), SQ7-1(6), and SQ7-1(1, 5) aptamers, which are internal 2'-O-methyl-modified aptamers prepared based on the SQ7-1 aptamer of the present disclosure. FIG. 12a depicts the areas of internal 2'-O-methyl-modification with rectangles, and FIG. 12b to FIG. 12d specifically disclose the nucleotide sequence for each area of internal 2'-O-methyl-modification.

FIG. 13a to FIG. 13d show the serum half-lives determined for the SQ7-1, SQ7-1(1), SQ7-1(5), and SQ7-1(1,5) aptamers of the present disclosure.

Figure 14:
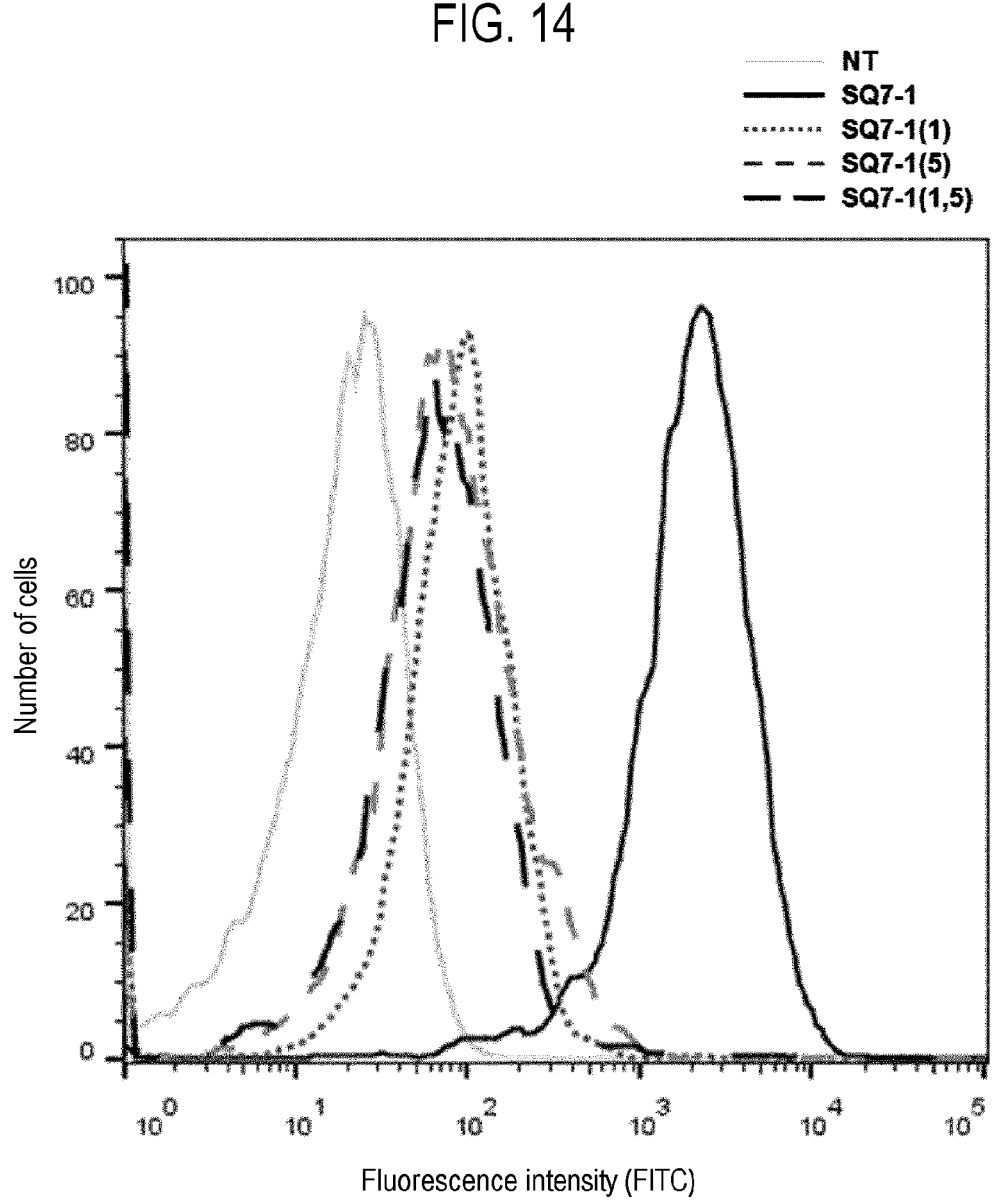

FIG. 14 shows target cell binding affinities of the SQ7-1, SQ7-1(1), SQ7-1(5), and SQ7-1(1,5) aptamers of the present disclosure determined with a flow cytometer.

Figure 15:
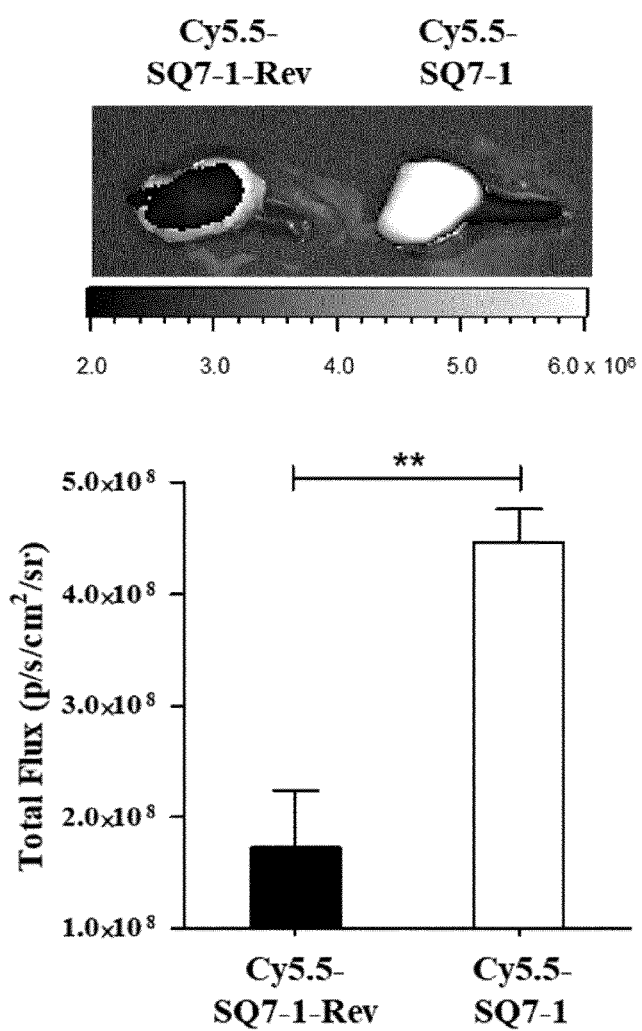

FIG. 15 shows targeting profile of the SQ7-1 aptamer of the present disclosure for pancreatic cancer tissue determined with bioluminescence imaging in a xenograft mouse model for pancreatic cancer cells of a human pancreatic cancer patient.

Figure 16A:
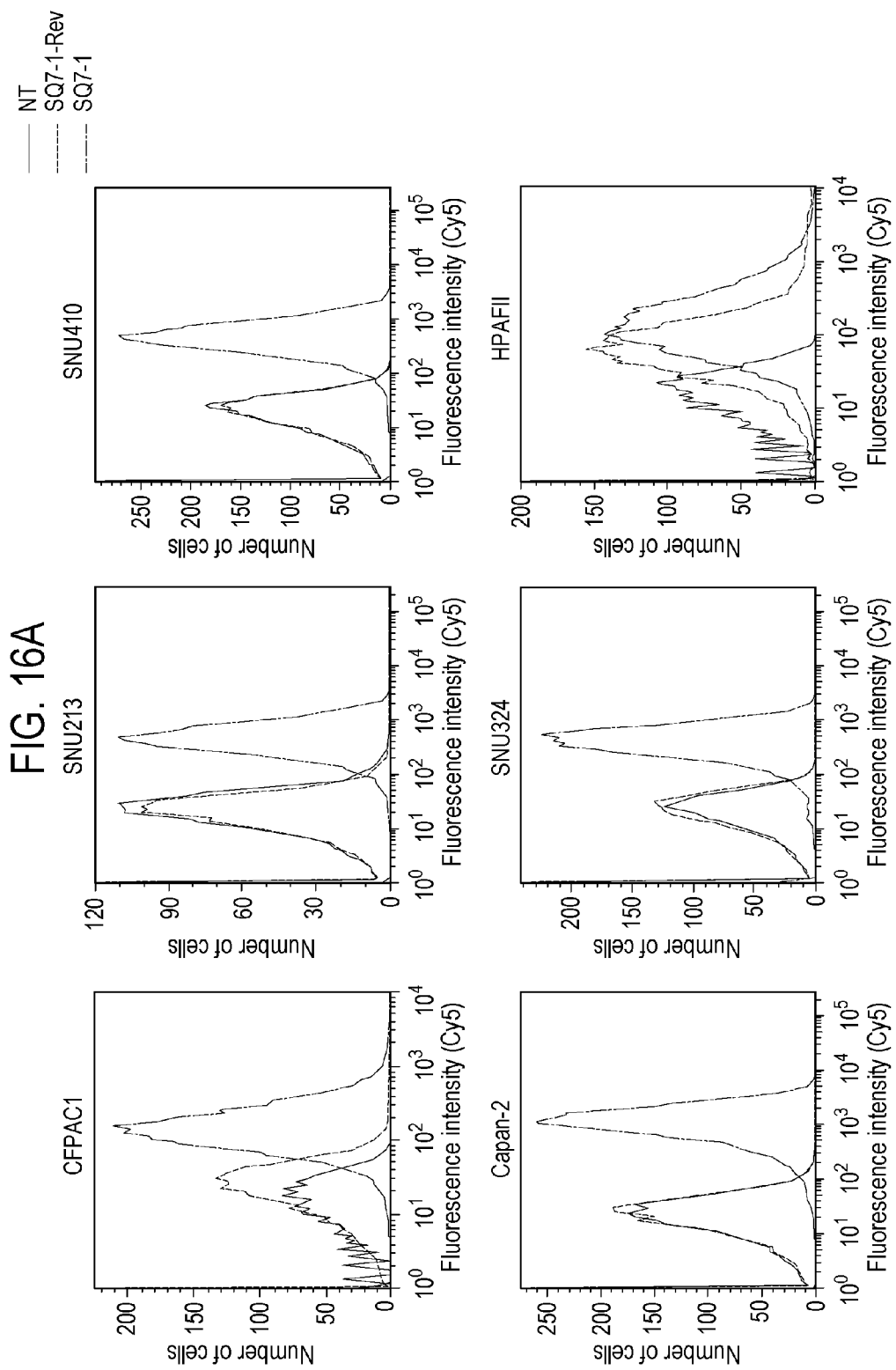

FIG. 16a and FIG. 16b show binding affinities of the SQ7-1 aptamer of the present disclosure to various pancreatic cancer cell lines determined with a flow cytometer (FACS).

Figure 17:
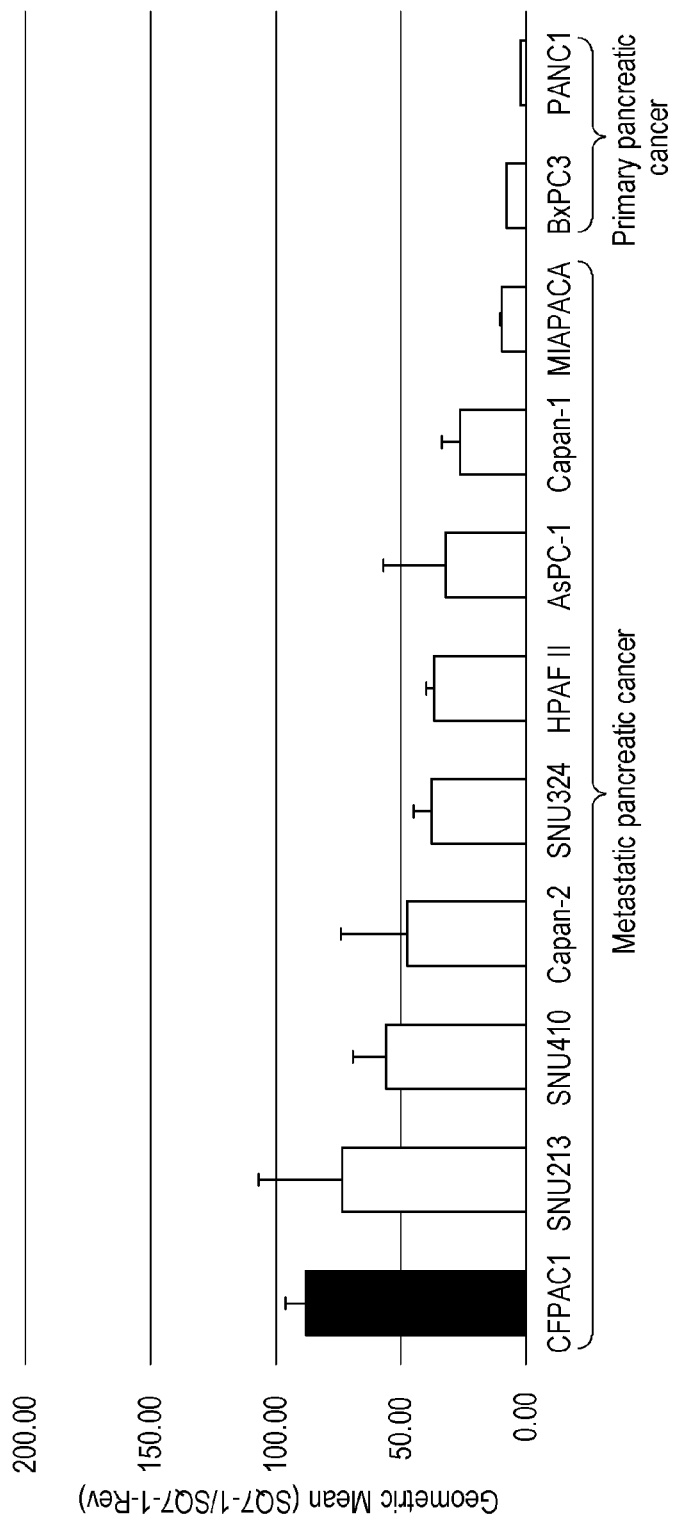

FIG. 17 shows the geometric means of the relative fluorescence intensities of the SQ7-1 aptamer over the SQ7-1-Rev aptamer in number of folds, based on the results given in FIG. 16.

Figure 18:
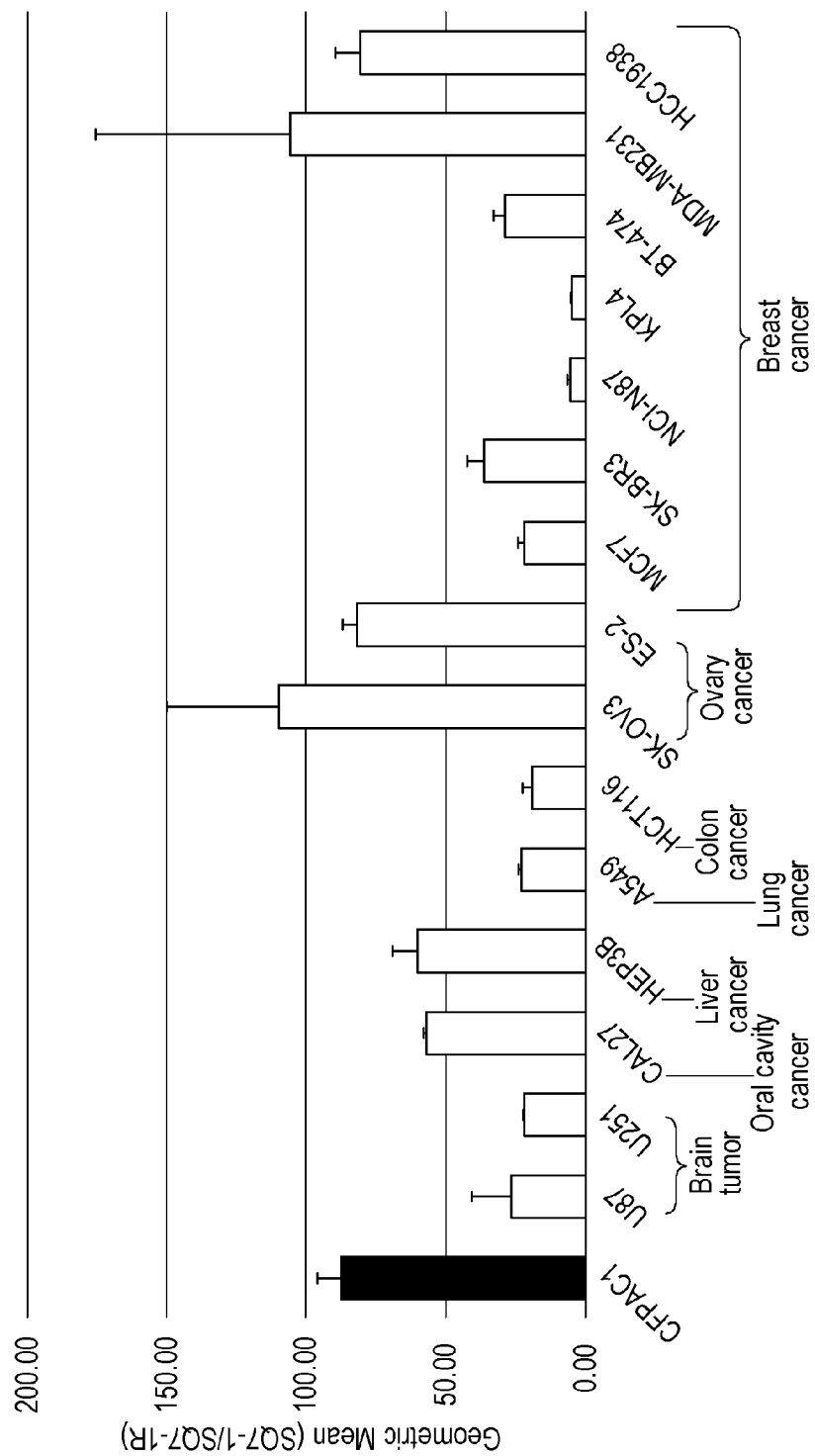

FIG. 18 shows the geometric means of the relative fluorescence intensities of the SQ7-1 aptamer over the SQ7-1-Rev aptamer in number of folds, based on the binding affinities of the SQ7-1 aptamer of the present disclosure to various cancer cell lines determined with a flow cytometer (FACS).

Figure 19:
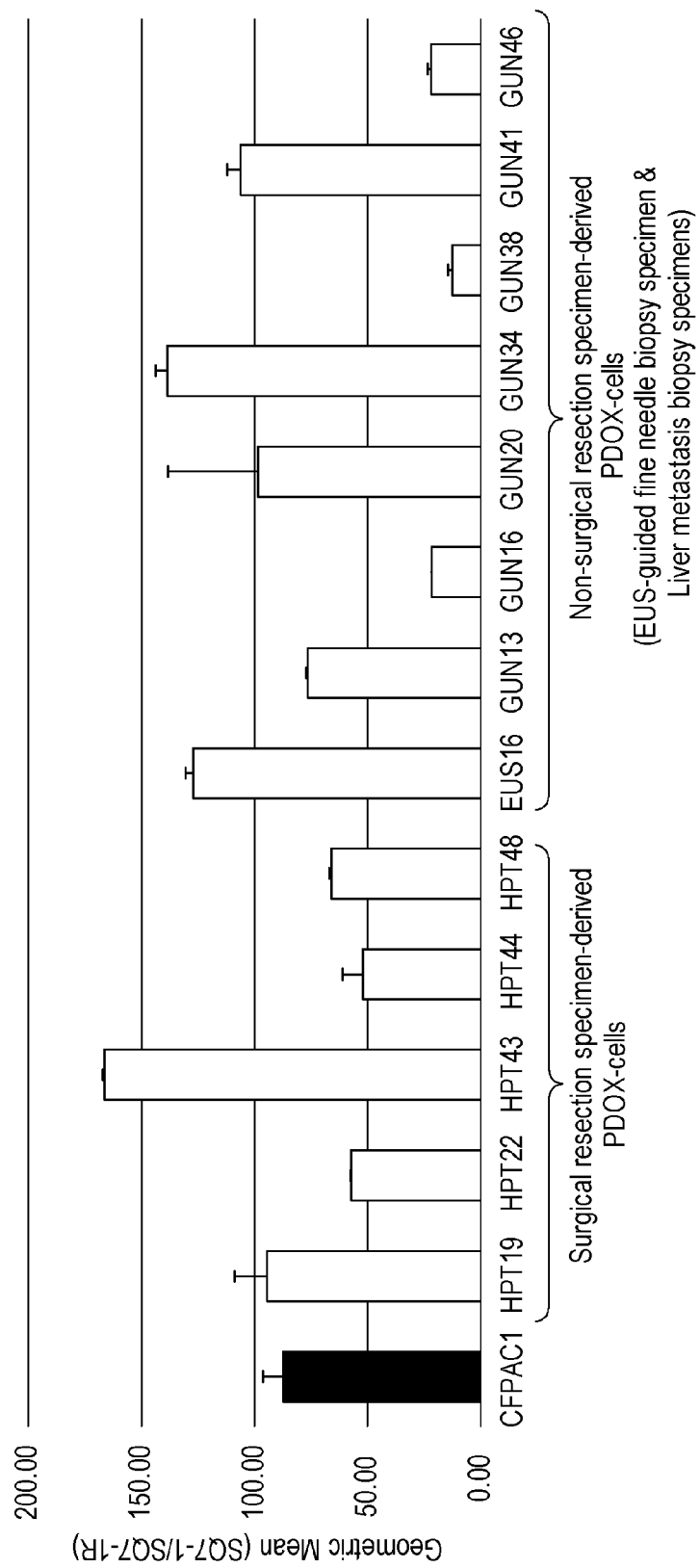

FIG. 19 shows the geometric means of the relative fluorescence intensities of the SQ7-1 aptamer over the SQ7-1-Rev aptamer in number of folds, based on the binding affinities of the SQ7-1 aptamer of the present disclosure to various pancreatic cancer PDOX-derived cell lines determined with a flow cytometer (FACS).

DETAILED DESCRIPTION

The present disclosure will be clearly understood from the aspects described above and Experimental Examples or Examples described below. In the following, the present disclosure will be explained in detail such that a person of ordinary skill in the art can easily understand and reproduce the disclosure, by way of working examples described in reference to accompanying tables. However, the Experimental Examples or Examples described below are given just to illustrate the present disclosure and the scope of the present disclosure is not limited to such Experimental Examples or Examples.

Experimental Example 1 Aptamer Screening Using Cell-SELEX

Experimental procedures for screening of aptamers that specifically bind to pancreatic cancer cells using the Cell-SELEX technique are schematically illustrated in FIG. 3.

Specifically, to obtain a cell line expressing cell membrane proteins characteristic of pancreatic cancer, pancreatic cancer cells were transplanted into an animal model and pancreatic cancer cell line CMLu-1 was isolated from a tissue to which the cancer had metastasized (FIG. 3A).

A ssDNA library was prepared and then screened using cells of the pancreatic cancer cell line CMLu-1 as the target cells (positive cells) and hTERT/HPNE cells (Human Pancreatic Nestin Expressing cells) as the control cells (negative cells). Selection of ssDNA molecules which bind only to the pancreatic cancer cells and not to the control cells was iterated for multiple rounds, and the resulting enriched ssDNA pool was cloned and sequenced, followed by clustering.

(1) Construction of a Metastatic Pancreatic Cancer Cell Line from a Xenograft Mouse Model of a Human Pancreatic Cancer Cell Line The metastatic pancreatic cancer cell line CMLu-1 was obtained as described below. An orthotopic mouse model was built using NOD/SCID mouse. First, to construct an animal model that can mimic metastasis of pancreatic cancer, a pancreatic cancer cell line stably expressing the firefly luciferase (CFPAC-1-Luci) was established and used to enable non-invasive monitoring of tumorigenesis over time. CFPAC-1-Luci pancreatic cancer cells were transplanted orthotopically into a NOD/SCID mouse. After 43 days, tumor tissue was removed from the lung tissue of the mouse where pancreatic cancer had metastasized, and the isolated tumor tissue was genotyped, showing that the genetic attributes of the metastatic tumor cells are identical to those of the pancreatic cancer cells. Then, single cells were prepared from the tumor tissue and cultured. CMLu-1 cells isolated from the metastatic tumor tissue were cultured and maintained in RPMI-1640 medium (Hyclone, Logan, UT, USA) plus 10% FBS (Thermo Fisher Scientific, USA) and 100 IU/mL of Anti-Anti (antibiotic-antimycotic; Gibco).

The resulting CMLu-1 cells were used as the cells for positive selection in Cell-SELEX, and human pancreatic duct normal epithelial cells (HPNE) purchased from ATCC Inc. were used as the control cells for negative selection.

(2) Preparation of a ssDNA Library and Primers for Cell-SELEX

Figure 1:
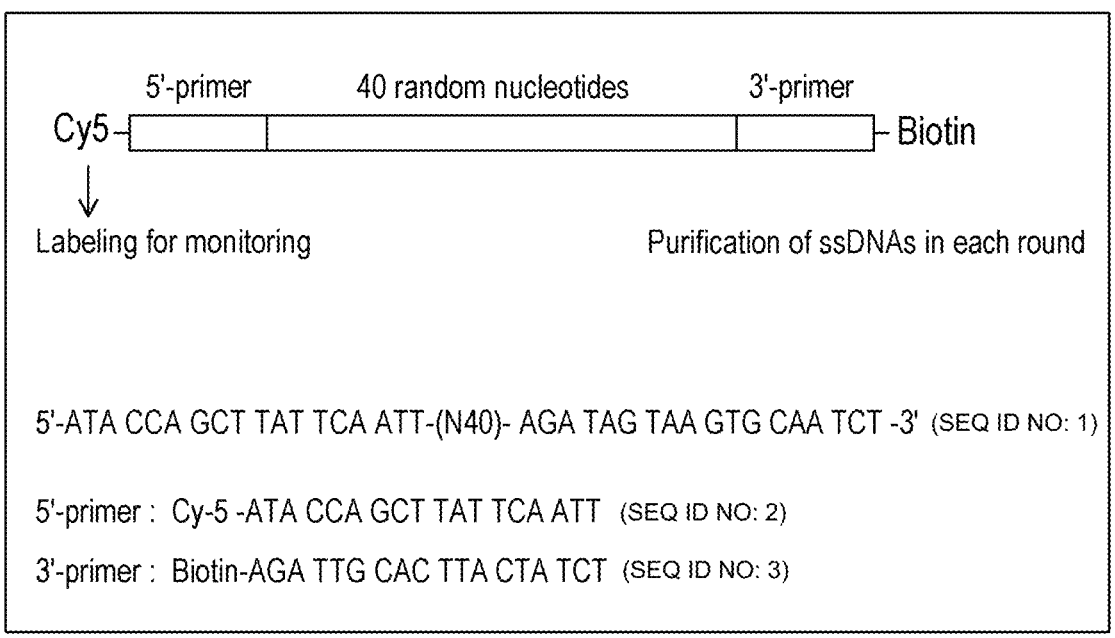
FIG. 1 illustrates the format of the nucleotide sequences included in the DNA library of the present disclosure as well as the formats of the forward primer and reverse primer that can be used to amplify or identify the above nucleotide sequences. Specifically, the nucleotide sequences in the DNA library comprise 20 constant nucleotides at the 5'-terminus, 40 random nucleotides in the middle, and additional 20 constant nucleotides at the 3'-terminus. The forward primer is labeled with Cy5 at its 5'-terminus (5'-Cy5-sequence-3'), and the reverse primer with biotin at its 5'-terminus (5'-biotin-sequence-3').

The DNA library used in Cell-SELEX for pancreatic cancer-specific aptamers was a pool of DNA sequences that are composed of a combination of constant and unique nucleotides. The DNA sequences comprised 20 constant nucleotides at the 5'-terminus, 40 random nucleotides in the middle, and additional 20 constant nucleotides at the 3'-terminus. 5'-terminus of the DNA sequences was labeled with Cy5 in order to monitor enrichment of selection using a fluorescence-activated cell sorter ("FACS"; so-called "flow cytometer"), and the 3'-terminus was labeled with biotin for purification of the ssDNA molecules (FIG. 1). In addition, the forward primer was labeled with Cy5 at its 5'-terminus (5'-Cy5-sequence-3'), and the reverse primer with biotin at its 5'-terminus (5'-biotin-sequence-3'). The compositions of DNAs included in the DNA library as well as the forward and reverse primers are as shown in Table 1 below.

TABLE 1

| | |
|---|---|
| Format of DNA library nucleotides (SEQ ID NO: 1) | 5'-ATA CCA GCT TAT TCA ATT-[nucleotides 40(N40)]-AGA TAG TAA GTG CAA TCT-3' |
| Forward primer; 5'-primer (SEQ ID NO: 2) | 5'-Cy5-ATA CCA GCT TAT TCA ATT-3' |

TABLE 1-continued

Reverse primer; 3'- 5'-biotin-AGA TTG CAC TTA CTA TCT-3'
primer (SEQ ID NO: 3)

PCR was used to amplify eluted DNA pools. ssDNAs were isolated by capturing biotinylated complementary strands using the streptavidin-biotin bond and denaturing double-stranded DNAs with NaOH. PCR mixes were prepared, and PCR was carried out as instructed by the manufacturer.

(3) Library Screening Through Cell-SELEX

The ssDNA library prepared as described above was screened using CMLu-1 cells as the target cells (positive cells) and hTERT/HPNE cells as the control cells (negative cells). 10 nmol of the DNA library was dissolved in 1,000 μL of a binding buffer (Dulbecco's PBS (Hyclone, USA) with 5 mM $MgCl_2$, 0.1 mg/mL tRNA, and 1 mg/mL BSA). The DNA library or enriched pool was denatured at 95° C. for 10 min and cooled on ice for 10 min, followed by incubation with CMLu-1 cells in an orbital shaker at 4° C. for 1 hour.

The CMLu-1 cells were then washed 3 times to remove unbound DNA sequences, and the bound DNA molecules were eluted via centrifuge using 1,000 μL of a binding buffer at 95° C. for 15 min. To carry out a counter selection, an aptamer pool was incubated with hTERT/HPNE cells for 1 hour, after which the supernatant was collected for negative selection. The enriched pools were monitored using FACS, and Quiagen's cloning kit for sequencing (Quiagen, Germany) was used for cloning into *Escherichia coli* to identify aptamer candidates.

(4) Cloning and Sequencing of Enriched ssDNA Pool and Multiple Sequence Alignment For selection of candidate sequences, the enriched ssDNA pool after 5 rounds was cloned and sequenced. The ssDNA pool was amplified by PCR using unmodified primers, ligated to pGEM-T easy vector (Promega, USA), and then cloned into HIT™-DH5a competent cells (Promega, USA). Thereafter, 200 cloned sequences were analyzed by Cosmogenetech Inc. (Seoul, Korea) and aligned using ClustalX 1.83.

Figure 2:
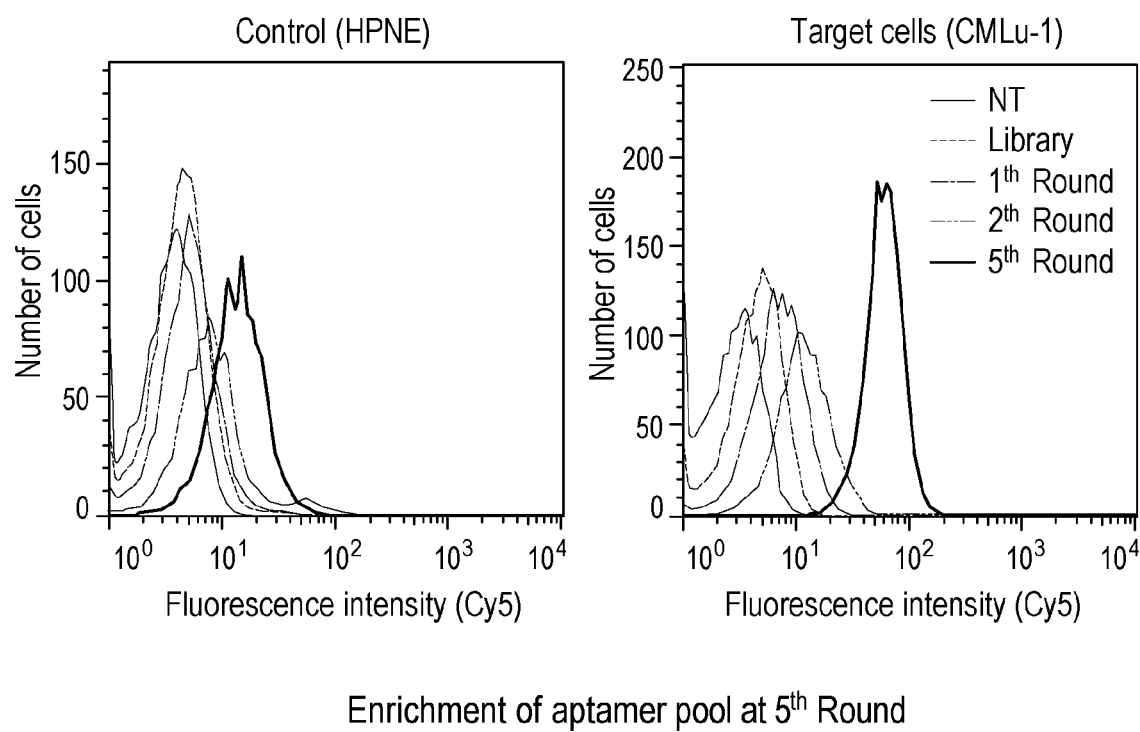
FIG. 2 shows the results of enriching a ssDNA pool, out of the DNA library of the present disclosure, which has binding affinity to pancreatic cancer cells and determining with a flow cytometer (Fluorescence-activated cell sorting; FACS) whether the cell binding affinity of the pool is increased according to the number of rounds.

The extent of enrichment according to the number of rounds of selection is as illustrated in FIG. 2.

The process described above in (1) to (4) is schematically illustrated in FIG. 3. Aptamers sequenced through the above process were clustered into aptamers with similar sequences. As a result, eleven Cy5-labeled aptamer family candidates (SQ1 to SQ11) were identified. The contents of individual aptamer families in the entire pool were as shown in Table 2 below.

TABLE 2

| Aptamer family | Content in enriched DNA pool (%) |
| --- | --- |
| SQ1 | 14.09 |
| SQ2 | 13.42 |
| SQ3 | 5.37 |
| SQ4 | 4.70 |
| SQ5 | 4.70 |
| SQ6 | 3.36 |
| SQ7 | 2.01 |
| SQ8 | 2.68 |
| SQ9 | 1.34 |
| SQ10 | 1.34 |
| SQ11 | 1.34 |

Experimental Example 2 Determination of Target Cell Binding Specificity of Enriched Aptamer Family Candidates The CMLu-1 target cell binding specificities of the enriched aptamer family candidates obtained in (4) of Experimental Example 1 were determined with flow cytometry (FACS).

Each Cy5-labeled aptamer family candidate was incubated, along with $3 \times 10^5$ CMLu-1 cells and hTERT/HPNE cells, in the binding buffer used for Cell-SELEX at 4° C. for 1 hour. The cells were washed 3 times with binding buffer containing 0.1% $NaN_3$, and the pellets having bound sequences were resuspended in the binding buffer. Fluorescence-based assay was carried out on 10,000 cells using BD FACSCallibur™ and FACSVerse™ (BD Biosciences, USA), and the data were analyzed using FlowJo software v10.0.7.

The results from the determination of target cell binding affinity of individual Cy5-labeled aptamer family candidates are shown in FIG. 4. The aptamer with the highest binding specificity for metastatic pancreatic cancer cells (CMLu-1), the target cells, was identified as SQ7, whose sequence is shown below.

*SQ7 aptamer sequence
(SEQ ID NO: 4)
5'-AGCAGCACAGAGGTCAGATGATGTTGGTATATACTTCTTTAGCTTG
GAACCAACTCTTGCCCTATGCGTGCTACCGTGAA-3'

The aptamer sequences included in the SQ7 family are listed in the following table.

TABLE 3

Sequences of SQ7 and SQ7-subtypes

| Aptamer | Sequence | Number | % |
| --- | --- | --- | --- |
| SQ7 | AGCAGCACAGAGGTCAGATGATGTTGGTATATACTT CTTTAGCTTGGAACCAACTCTTGCCCTATGCGTGCTA CCGTGAA | 3 | 4.03 |
| SQ7a | AGCAGCACAGAGGTCAGATGATGTTGGTATATACTT CTTTAGCTTGGAACCAACTCTT<u>CT</u>CCTATGCGTGCTA CCGTGA (SEQ ID NO: 15) | 1 | |

TABLE 3-continued

Sequences of SQ7 and SQ7-subtypes

| Aptamer | Sequence | Number | % |
|---|---|---|---|
| SQ7b | AGCAACACAGAGGTCAGATGATGTTGGTATATACTT CTTTAGCTTGGAACCCACTCTTGTCCTATGCGTGCTA CCGTGAA (SEQ ID NO: 16) | 2 | |

Experimental Example 3 Analysis of SQ7 Aptamer and Functional Characterization of Aptamer Fragments The secondary structure determined for the SQ7 aptamer selected in Example 2 is as shown in FIG. 5. In addition, to confirm the cell binding affinity, the SQ7 aptamer and, as controls, no-treatment control (NT), the DNA pool library and the SQ8-Comp aptamer (an aptamer having a nucleotide sequence partly complementary to the SQ8 aptamer; SEQ ID NO: 5) were prepared and their target cell binding was determined in the same manner as in Experimental Example 2 using FACS. As demonstrated in FIG. 6, the results show that whereas the controls, i.e., NT, the DNA pool library, and the SQ8-Comp aptamer, had low binding affinities of similar levels, the SQ7 aptamer exhibited a remarkably superior target cell binding affinity.

In order to determine whether some portions of the SQ7 aptamer are critical for the pancreatic cancer-specific binding, various aptamers comprising parts of the SQ7 aptamer were prepared and their binding affinity to the target cell was investigated. If the length of an aptamer can be reduced while retaining its cell binding affinity, it is likely that aptamer production costs are reduced while cell penetration is enhanced. The results demonstrated that the SQ7-1 aptamer having the sequence indicated in Table 4 below is superior in terms of endocytosis while almost fully retaining the target cell binding affinity. Given the above results, target cell binding affinities of the SQ7 aptamer, the SQ7-1 aptamer, NT, the DNA pool library, and the SQ8-Comp aptamer were determined in the same manner as in Experimental Example 2 using FACS. As demonstrated in FIG. 6b, the results show that whereas the controls, i.e., NT, the DNA pool library, and the SQ8-Comp aptamer, had low binding affinities of similar levels, the SQ7-1 aptamer exhibited, like the SQ7 aptamer, a remarkably superior target cell binding affinity.

The nucleotide sequence of the SQ7-1 aptamer is shown below (SEQ ID NO: 6), and the corresponding secondary structure is shown in FIG. 7. In addition, SQ7-1-Rev aptamer (an aptamer having the sequence of the SQ7-1 in the reverse direction; SEQ ID NO: 7) was prepared in order to use it as a control for the SQ7-1 aptamer in subsequent experiments.

Experimental Example 4 Determination of Efficient Targeting of the Selected Aptamer into Cells and Tissues (1) Endocytosis Efficiencies of Selected Aptamers were Determined by Confocal Microscopy Imaging.

$1\times10^4$ cells/well of control cells (HPNE) and target cells (CMLu-1) were plated on 8-well chamber slides (Thermo scientific, USA) coated with poly-L-lysine (Sigma, USA) 4 hours prior to the experiment. Upon washing with a washing buffer, Cy5-labeled aptamer (250 nM) or DNA pool library in 200 μl of binding buffer at 4° C. was added and incubated. After washing twice, the cells were fixed using 4% paraformaldehyde, followed by staining of the nucleus with Hoechst33342. Thereafter, the cells were subjected to imaging by confocal microscopy (LSM780, Carl Zeiss, Germany), and the images thus obtained were analyzed with Zen blue edition software.

Results of confocal microscopy on the SQ7 and SQ7-1 aptamers are as shown in FIGS. 8 and 9. The brightest looking, white areas in the pictures represent regions heavily populated with aptamers. As seen in FIGS. 8 and 9, the SQ7 and SQ7-1 aptamers targeted pancreatic cancer cells over the control cells and showed excellent levels of endocytosis (internalization) into the cells.

(2) Determination of Pancreatic Cancer Targeting by Aptamers Through In Vivo and Ex Vivo Fluorescence Imaging Female Hsd: Athymic nude-Foxn1 nude mice aged 6 weeks were purchased from Harlan Laboratories, Inc. (France). The mice were housed in a specific pathogen free (SPF) environment under controlled conditions of light and humidity, with their food and water supplied by the NCC animal facility. All animal studies were reviewed and approved by the Institutional Animal Care and Use Committee (IACUC) of the National Cancer Center Research Institute (NCCRI) (NCC-16-247). The NCCRI is a facility accredited by the Association for Assessment and Accreditation of Laboratory Animal Care International (AAALAC International).

An orthotopic xenograft mouse model of pancreatic cancer was constructed by injecting CFPAC-1 cells ($1\times10^6$ cells) purchased from the ATCC into the tail of mouse pancreas. At 3 weeks after inoculation, mice were divided into two groups according to the treatment to be given

TABLE 4

| Aptamer | Sequence |
|---|---|
| SQ7 | 5'-AGCAGCACAGAGGTCAGATGATGTTGGTATATACTTCTTTAGCTT GGAACCAACTCTTGCCCTATGCGTGCTACCGTGAA-3' |
| SQ7-1 | 5'-GTTGGTATATACTTCTTTAGCTTGGAACCAAC-3' (SEQ ID NO: 6) |
| SQ7-1-Rev | 5'-CAACCATATATGAAGAAATCGAACCTTGGTTG-3' (SEQ ID NO: 7) |

(Cy5.5-SQ8-Comp aptamer vs Cy5.5-SQ7 aptamer or Cy5.5-SQ7-1-Rev aptamer vs Cy5.5-SQ7-1 aptamer), followed by intravenous administration of a Cy5.5-labeled aptamer (300 pmol/50 µl PBS) mentioned above.

For ex vivo experiments, mice were sacrificed 15 min or 3 hours after administration and then dissected. Tumor tissues were removed and subjected to bioluminescence imaging using IVIS Lumina (Caliper Life Science, Hopkinton, MA, USA). All image data were analyzed using Living Image Acquisition and Analysis software.

The gray-scale pictures in FIGS. 10 and 11 show the results of bioluminescence imaging for the SQ7 and SQ7-1 aptamers. Total flux obtained from the imaging results are plotted in FIGS. 10 and 11.

Experimental Example 5 Preparation and Identification of Modifications for Enhanced Serum Stability of Aptamers Based on the SQ7-1 aptamer prepared in the experimental example described above, internal 2'-O-methyl-modified aptamers were prepared in order to enhance serum stability of the aptamer. Specifically, SQ7-1(1), SQ7-1(2), SQ7-1(3), SQ7-1(4), SQ7-1(5), SQ7-1(6), and SQ7-1(1, 5) aptamers were prepared by modifying different regions in the secondary structure of the SQ7-1 aptamer (FIGS. 12a to 12d).

The nucleotide sequences of the resulting internal 2'-O-methyl-modified aptamers are summarized in Table 5 below.

TABLE 5

| Aptamer | Sequence | Number of 2'-O-methyl-modified [A, G, C, U] |
|---|---|---|
| SQ7-1 | 5'-GTTGGTATATACTTCTTTAGCTTGGAACCAAC-3' (SEQ ID NO: 6) | 0 |
| SQ7-1(1) | 5'-[2'-O-Methyl(G)][2'-O-Methyl(U)][2'-O-Methyl(U)][2'-O-Methyl(G)][2'-O-Methyl(G)][2'-O-Methyl(U)]ATATACTTCTTTAGCTTGGAACCAAC-3' (SEQ ID NO: 8) | 6 |
| SQ7-1(2) | GTTGGT[2'-O-Methyl(A)][2'-O-Methyl(U)][2'-O-Methyl(A)][2'-O-Methyl(U)][2'-O-Methyl(A)]CTTCTTTAGCTTGGAACCAAC (SEQ ID NO: 9) | 5 |
| SQ7-1(3) | GTTGGTATATACT[2'-O-Methyl(U)][2'-O-Methyl(C)][2'-O-Methyl(U)][2'-O-Methyl(U)][2'-O-Methyl(U)]AGCTTGGAACCAAC (SEQ ID NO: 10) | 5 |
| SQ7-1(4) | GTTGGTATATACTTCTTTAG[2'-O-Methyl(C)][2'-O-Methyl(U)][2'-O-Methyl(U)][2'-O-Methyl(G)][2'-O-Methyl(G)][2'-O-Methyl(A)]ACCAAC (SEQ ID NO: 11) | 6 |
| SQ7-1(5) | GTTGGTATATACTTCTTTAGCTTGGA[2'-O-Methyl(A)][2'-O-Methyl(C)][2'-O-Methyl(C)][2'-O-Methyl(A)][2'-O-Methyl(A)][2'-O-Methyl(C)] (SEQ ID NO: 12) | 6 |
| SQ7-1(6) | GTTGGT[2'-O-Methyl(A)][2'-O-Methyl(U)][2'-O-Methyl(A)][2'-O-Methyl(U)][2'-O-Methyl(A)][2'-O-Methyl(C)][2'-O-Methyl(U)][2'-O-Methyl(U)][2'-O-Methyl(C)][2'-O-Methyl(U)][2'-O-Methyl(U)][2'-O-Methyl(U)][2'-O-Methyl(A)][2'-O-Methyl(G)][2'-O-Methyl(C)][2'-O-Methyl(U)][2'-O-Methyl(U)][2'-O-Methyl(G)][2'-O-Methyl(G)][2'-O-Methyl(A)]ACCAAC (SEQ ID NO: 13) | 20 |
| SQ7-1(1,5) | [2'-O-Methyl(G)][2'-O-Methyl(U)][2'-O-Methyl(U)][2'-O-Methyl(G)][2'-O-Methyl(G)][2'-O-Methyl(U)]ATATACTTCTTTAGCTTGGA[2'-O-Methyl(A)][2'-O-Methyl(C)][2'-O-Methyl(C)][2'-O-Methyl(A)][2'-O-Methyl(A)][2'-O-Methyl(C)] (SEQ ID NO: 14) | 12 |

In the imaging results presented at the top of the above drawings, the brighter (whiter) a region appears, the greater the amount of aptamers bound to the cells in that region is. It can be seen that imaging results for the SQ7 and SQ7-1 aptamers appear whiter than those for other aptamers.

Thus, it has been demonstrated that the aptamers of the present disclosure move towards and bind specifically to pancreatic cancer tissue compared with other, control aptamers (SQ1 aptamer (SEQ ID NO: 17), SQ8-Comp aptamer, and SQ7-1-Rev aptamer) and have remarkably superior targeting efficiencies for pancreatic cancer tissues.

5 µg each of the internal 2'-O-methyl-modified aptamers thus prepared were incubated at 37° C. in mouse serum for 0, 0.1, 0.5, 2, 6, and 24 hours. At respective time points mentioned above, 0.5 M EDTA was added to the samples to inhibit DNase activity, followed by addition of EtOH-NaOAc to effect precipitation. Samples of DNA-aptamer-precipitates were analyzed with HPLC.

Chromatography was carried out with Waters e2695 HPLC system (MA, USA) equipped with the variable wavelength detector (VWD) QuatPump. A personal computer installed with Empower3 personal single system software for LC was used for processing of chromatographic data. Analysates were separated using Venusil, XBP C18 column (250 mm×4.6 mm, 5 µm) purchased from Agela Technologies Inc. (Beijing, China). The mobile phase was a methanol-water (55:45, by volume) mixture, and the flow rate was 0.5 mL/min. The column temperature was 30° C., and the wavelength for measurement was 260 nm. 15 µL LC microsyringes purchased from Shanghai GaoGe Industrial and Trading Co., Ltd. (Shanghai, China) were used for injection.

The results showed that the SQ7-1(1), SQ7-1(5), and SQ7-1(1,5) aptamers have significantly increased half-lives. Specifically, as seen in FIG. 13, the SQ7-1(1), SQ7-1(5), and SQ7-1(1,5) aptamers exhibited 91-fold, 145-fold, and 760-fold increases in half-life, respectively, relative to the SQ7-1 aptamer. The binding affinities of the above-mentioned aptamers to the target cells were slightly lower compared with the SQ7-1 aptamer but still distinctly higher than that of the DNA pool library (thin solid line farthest to the left in the graph) (FIG. 14).

To summarize, as described above, the DNA aptamers according to the present disclosure specifically bind to pancreatic cancer with high binding affinities. It was demonstrated that targeting efficiencies for the target cell or tissue can be increased by reducing the size of the selected aptamers, and serum stability can be increased through modifications enhancing resistance to DNase.

Experimental Example 6 Determination of Targeting in a Mouse Orthotopic Xenograft Model for Human Patient Pancreatic Cancer Tissue (Patient-Derived Orthotopic Xenograft Model; PDOX Model)

In order to determine whether the aptamers of the present disclosure exhibit excellent targeting efficiencies even in a PDOX model which can recapitulate the complexity and heterogeneity of patient tumor tissue, in vivo verification experiments were carried out using fluorescence imaging.

With the approval of the Institutional Review Board ("IRB") of the NCC, a patient-derived orthotopic xenograft (PDOX) model was established by collecting specimens from patients who submitted informed consent and directly transplanting them into the pancreas of a nude mouse (purchased from Harlan Laboratories, Inc. (France)). As for primary tumor specimens from pancreatic cancer patients (called "HPTs" below), right upon surgical resection, and in the case of patients with inoperable advanced pancreatic cancer, right after collection of specimens for liver metastasis tissue biopsy (called "GUNs" below) from the patients, specimens were transported in tubes containing a medium and transplanted as soon as possible into female Hsd: Athymic nude-FoxnI nude mice (obtained from the same source as in Experimental Example 4), by making an incision in the tail of pancreas and then closing the incision after transplantation (PDOX $1^{st}$ generation, F1). Thereafter, the size of tumor was measured periodically using abdominal palpation and MRI, and when the tumor attains a volume of 3000 mm$^3$, the mouse was sacrificed to obtain tumor tissue. Tumor tissue fragments of a certain size (3 mm*3 mm*3 mm) were then orthotopically re-implanted into multiple nude mice subjects to generate subsequent generations (F2, F3, F4.) and increase the number of subjects.

At the $4^{th}$ generation (F4), the established PDOX mouse model was divided into two groups of three subjects, and the individual groups were given intravenously either the SQ7-1 aptamer or the SQ7-1-Rev aptamer, in the form of Cy5.5-labeled aptamer (300 pmol/50 µl PBS). 15 min after the administration, the mice were sacrificed and dissected to remove tumor tissues, which were then subjected to bioluminescence imaging using IVIS Lumina (Caliper Life Science, Hopkinton, MA, USA). All image data were analyzed using Living Image Acquisition and Analysis software. The gray-scale picture in FIG. 15 shows the results of bioluminescence imaging. Total flux obtained from the imaging results are plotted in FIG. 15.

As in FIGS. 10 and 11, in the imaging results presented at the top of FIG. 15 also, the brighter (whiter) a region appears, the greater the amount of aptamers bound to the cells in that region is. It can be seen that the SQ7-1 aptamer gives a much whiter image than the SQ7-1-Rev aptamer.

Thus, it has been demonstrated that the aptamers of the present disclosure have remarkably superior targeting efficiencies even in a PDOX model which retains the complexity and heterogeneity of patient tumor tissue.

Experimental Example 7 Determination of Binding Affinity in Various Pancreatic cancer cell lines Additional flow cytometry (FACS) assays were carried out to determine the binding affinity of the aptamers of the present disclosure to various pancreatic cancer cell lines.
[Preparation of an Antibody Binding Aptamer]

To prepare an antibody binding aptamer, 250 nM digoxigenin-labeled SQ7-1 aptamer and 125 nM anti-digoxigenin antibody (Abcam; Cat. No. ab420, USA) were admixed at room temperature for 30 min.

Flow cytometry was carried out in the same manner as in Experimental Example 2, with the exception that the antibody binding aptamer prepared as describe above was used, and Alexa 488-labeled anti-mouse IgG (Invitrogen, USA) was used as the secondary antibody, at a concentration of 4 g/ml. Cells from CFPAC-1 cell line, SNU-213 cell line, SNU-410 cell line, Capan-2 cell line, HPAF-II cell line, AsPC-1 cell line, Capan-1 cell line, MIA PaCa cell line, BxPC-3 cell line, and PANC-1 cell line were used. All of the above-mentioned cell lines were purchased from the ATCC.

Results from the determination of binding affinity of the aptamers to various pancreatic cancer cell lines are shown in FIGS. 16 and 17. FIG. 17 shows the geometric means of the relative fluorescence intensities of the SQ7-1 aptamer over the SQ7-1-Rev aptamer in number of folds.

According to the results shown in FIGS. 16 and 17, the SQ7-1 aptamer of the present disclosure binds more efficiently and specifically to all the pancreatic cancer cell lines compared with the SQ7-1-Rev aptamer. Taken together with the results of Experimental Examples 4 and 6 discussed above, it can be seen that the aptamers of the present disclosure would specifically bind to various types of pancreatic cancer cells.

In addition, the SQ7 aptamer similarly would specifically bind to various types of pancreatic cancer cells as it comprises the SQ7-1 aptamer sequence.

Experimental Example 8 Determination of Binding Affinity in Various Tumor Cell Lines Additional flow cytometry (FACS) assays were carried out to determine the binding affinity of the aptamers of the present disclosure to various tumor cell lines.

Flow cytometry was carried out in the same manner as in Experimental Example 2, with the exception that the same antibody binding aptamer and secondary antibody as used in Experimental Example 7 were used. Cells from U87 cell line, U251 cell line, CAL27 cell line, HEP3B cell line, A549 cell line, HCT116 cell line, SK-OV3 cell line, ES-2 cell line, MCF7 cell line, SK-BR3 cell line, NCI-N87 cell line, KPL4 cell line, BT-474 cell line, MDA-MB231 cell line, and HCC1938 cell line were used. All of the above-mentioned cell lines were purchased from the ATCC.

Results from the determination of binding affinity of the aptamers to various cancer cell lines are shown in FIG. 18. FIG. 18 shows the geometric means of the relative fluorescence intensities of the SQ7-1 aptamer over the SQ7-1-Rev aptamer in number of folds.

According to the results shown in FIG. 18, the SQ7-1 aptamer of the present disclosure binds more efficiently and specifically to various cancer cell lines such as colon cancer, liver cancer, lung cancer, brain tumor, oral cavity cancer, ovary cancer, and breast cancer cell lines, compared with the SQ7-1-Rev aptamer. Taken together with the results of Experimental Examples 4 and 6 discussed above, it can be seen that the aptamers of the present disclosure would specifically bind to various types of cancer cells.

In addition, the SQ7 aptamer similarly would specifically bind to various types of cancer cells as it comprises the SQ7-1 aptamer sequence.

Experimental Example 9 Determination of Binding Affinity in Pancreatic Ductal Adenocarcinoma PDOX-Derived Cell Lines Additional flow cytometry (FACS) assays were carried out to determine whether the aptamers of the present disclosure are likely to bind specifically to pancreatic cancer cells of clinical patients.

Unlike normal cells, which only have a limited number of cell divisions before death, cancer cells have the characteristic of infinite divisions. Accordingly, cancer cells isolated from tumor tissue are believed to be able to form a cell line capable of proliferating infinitely even in the absence of transfection and recapitulate clinical and molecular biological characteristics of the patient. In this experiment, tumor tissue removed from a pancreatic cancer PDOX mouse was divided into 3 mm*4 mm fragments, mixed with a human cell dissociation kit (Miltenyi Biotech Inc.) comprising collagenase, and reacted in a tissue dissociator (Gentle Macs, Miltenyi Biotech Inc) for 1 hour to separate the cells from connective tissue. Upon completion of the reaction, RPMI medium containing fetal bovine serum (FBS) was added to inhibit enzymatic activities, followed by centrifugation, to give precipitates of cells dissociated from tissue. The precipitates were suspended in RPMI medium containing FBS, and the cells were then plated evenly on 10 cm petri dishes to a level of $2 \times 10^6$ cells. The medium was replaced every other day while removing normal fibroblasts and dead cell, thereby establishing a PDOX-derived cancer cell line for each pancreatic cancer patient. The established cell lines were named in the same manner as the PDOX from which they were derived.

On cancer cell lines isolated from tumor tissues of PDOX models using liver metastasis patient biopsy tissues (GUN #13, GUN #16, GUN #20, GUN #34, GUN #38, GUN #41, and GUN #46), a PDOX model using endoscopic ultrasound-guided fine needle biopsy specimens (EUS #16), and PDOX models using surgical resection specimens (HPT #19, HPT #22, HPT #43, HPT #45, and HPT #48), flow cytometry was carried out in the same manner as in Experimental Example 2, with the exception that the same antibody binding aptamer as used in Experimental Example 7 was used.

Results from the determination of binding affinity of the aptamers to various PDOX-derived cell lines are shown in FIG. 19. FIG. 19 shows the geometric means of the relative fluorescence intensities of the SQ7-1 aptamer over the SQ7-1-Rev aptamer in number of folds.

According to the results shown in FIG. 19, the SQ7-1 aptamer of the present disclosure binds more efficiently and specifically to various PDOX-derived cell lines which have been derived from pancreatic cancer tissues collected from different patients, compared with the SQ7-1-Rev aptamer. Taken together with the results of Experimental Examples 4 and 6 discussed above, it can be seen that the aptamers of the present disclosure would specifically bind to pancreatic cancer tissue of clinical patients.

In addition, the SQ7 aptamer similarly would specifically bind to pancreatic cancer tissue of patients as it comprises the SQ7-1 aptamer sequence.

Although the technical idea of the present disclosure has been described above by referring to embodiments described in working examples and illustrated in the accompanying drawings, it should be noted that various substitutions, modifications, and changes can be made without departing from the technical idea and scope of the present disclosure which can be understood by a person of ordinary skill in the art to which the present disclosure pertains. In addition, it should be noted that that such substitutions, modifications and changes are intended to be encompassed by the scope of the appended claims.

What is claimed is:

1. A DNA aptamer consisting of 32 nucleotides and having the nucleobase sequence of SEQ ID NO: 6.

2. The DNA aptamer of claim 1, wherein the DNA aptamer has been modified to have resistance to DNase, wherein the modification is substitution of —OH group at 2' carbon of a sugar moiety in one or more nucleotides with -Me (methyl), —OMe, —NH2, —F (fluorine), —O-2-methoxyethyl-O-propyl, —O-2-methylthioethyl, —O-3-aminopropyl, —O-3-dimethylaminopropyl, —O—N-methylacetamido or —O-dimethylamidoxyethyl.

3. The DNA aptamer of claim 2, wherein the DNA aptamer, which has been modified to have resistance to DNase, has the nucleotide sequence of SEQ ID NO: 12.

4. A DNA aptamer consisting of the nucleotide sequence of SEQ ID NO: 4.

5. A DNA aptamer consisting of the nucleotide sequence of SEQ ID NO: 8.

6. A DNA aptamer consisting of the nucleotide sequence of SEQ ID NO: 14.

* * * * *